(12) United States Patent
Rao et al.

(10) Patent No.: US 8,148,158 B1
(45) Date of Patent: Apr. 3, 2012

(54) CALIX[4]ARENES FOR THE SELECTIVE DETECTION OF $ZN^{2+}$

(75) Inventors: Chebrolu Pulla Rao, Mumbai (IN); Rakesh Kumar Pathak, Mumbai (IN)

(73) Assignee: Indian Institute of Technology Bombay, Mumbai (IN)

( * ) Notice: Subject to any disclaimer, the term of this patent is extended or adjusted under 35 U.S.C. 154(b) by 0 days.

(21) Appl. No.: 13/023,027

(22) Filed: Feb. 8, 2011

(51) Int. Cl.
    *G01N 33/20* (2006.01)
(52) U.S. Cl. .............................. 436/81; 436/73; 436/74
(58) Field of Classification Search ............ 436/73, 436/81, 74
    See application file for complete search history.

(56) References Cited

OTHER PUBLICATIONS

Chang, K-C et al., "Triazole-Modified Calix[4]crown as a Novel Fluorescent On-Off Switchable Chemosensor," *Org. Lett.*, Jul. 25, 2007, vol. 9, No. 17, pp. 3363-3366.

Folin, M. et al., "Zinc content of normal human serum and its correlation with some hematic parameters," *BioMetals*, 1994, vol. 7, pp. 75-79.

(Continued)

*Primary Examiner* — Jill Warden
*Assistant Examiner* — Dwan A Gerido
(74) *Attorney, Agent, or Firm* — Foley & Lardner LLP

(57) ABSTRACT

Calix[4]arenes of Formula I are useful for selectively detecting $Zn^{2+}$ ion.

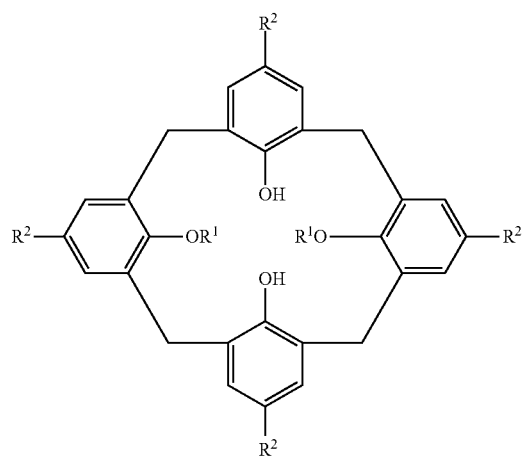

20 Claims, 10 Drawing Sheets

OTHER PUBLICATIONS

Frederickson, C.J. et al., "A quinoline fluorescence method for visualizing and assaying the histochemically reactive zinc (bouton zinc) in the brain," *J. Neuroscience Methods*, 1987, vol. 20, pp. 91-103.

Roney, N. et al., "ATSDR evaluation of the health effects of zinc and relevance to public health," *Toxicology and Industrial Health*, 2006, vol. 22, pp. 423-493.

Sorenson, M.B. et al. "Ultrastructural localization of zinc ions in the rat prostate: An autometallographic study," *The Prostate*, 1997, vol. 31, pp. 125-130.

Sugarman, B., "Zinc and Infection," *Reviews of Infectious Diseases*, Jan.-Feb. 1983, vol. 5, No. 1, pp. 137-147.

Bagatin, I.A. et al., "Mixed 8-oxyquinolinecalix[4]arene/phenanthroline receptors as luminescence sensors for zinc(II) ions," Inorg. Chem. Commun., 2003, vol. 6, pp. 288-293.

Barrios, A.M., "Intracellular Metal Detectors," ACS Chem. Biol., Mar. 17, 2006, vol. 1, No. 2, pp. 67-68.

Bitanihirwe, B.K.Y. et al., "Zinc: The Brain's Dark Horse," SYNAPSE, 2009, vol. 63, pp. 1029-1049.

Buie, N.M. et al., "New Fluorogenic Dansyl-Containing Calix[4]arene in the *Partial Cone* Conformation for Highly Sensitive and Selective Recognition of Lead(II)," Inorg. Chem., Mar. 18, 2008, vol. 47, pp. 3549-3558.

Bush, A.I. et al., "The galvanization of Beta-amyloid in Alzheimer's disease," Proc. Natl. Acad. Sci., May 28, 2002, vol. 99, No. 11, pp. 7317-7319.

Callan, J.F. et al., "Luminescent sensors and switches in the early 21st century," Tetrahedron, 2005, vol. 61, pp. 8551-8588.

Cox, E.H. et al., "Zinc-dependent protein folding," Curr. Opin. Chem. Biol., 2000, vol. 4, pp. 162-165.

Crivat, G. et al., "Fluorescence-Based Zinc Ion Sensor for Zinc Ion Release from Pancreatic Cells," Anal. Chem., Aug. 15, 2006, vol. 78, pp. 5799-5804.

Danscher, G. et al., "Zinc-specific Autometallographic In Vivo Selenium Methods: Tracing of Zinc-enriched (ZEN) Terminals, ZEN Pathways, and Pools of Zinc Ions in a Multitude of Other ZEN Cells," J. Histochem. Cytochem., 2005, vol. 53, No. 2, pp. 141-153.

Dennis, A.E. et al., "'Turn-on' fluorescent sensor for the selective detection of zinc ion by a sterically-encumbered bipyridyl-based receptor," Chem. Commun., 2007, pp. 4641-4643.

de Silva, A. P. et al., "Combining luminescence, coordination and electron transfer for signalling purposes," Coord. Chem. Rev., 2000, vol. 205, pp. 41-57.

de Silva, A. P. et al., "Signaling Recognition Events with Flourescent Sensors and Switches," Chem. Rev., Aug. 5, 1997, vol. 97, pp. 1515-1566.

Dessingou, J. et al., "A direct fluorescence-on chem-sensor for selective recognition Zn(II) by a lower rim 1,3-di-derivative of calix[4]arene possessing bis-{N-(2-hydroxynaphthyl-1-methylimine)} pendants," Tetrahedron Letters, Sep. 30, 2005, vol. 46, pp. 7967-7971.

Domaille, D.W. et al., "Synthetic fluorescent sensors for studying the cell biology of metals," Nat. Chem. Biol., Mar. 2008, vol. 4, No. 3, pp. 168-175.

Esqueda, A.C. et al., "A New Gadolinium-Based MRI Zinc Sensor," J. Am. Chem. Soc., Jul. 24, 2009, vol. 131, pp. 11387-11391.

Frederickson, C.J. et al., "Depletion of Intracellular Zinc from Neurons by Use of an Extracellular Chelator In Vivo and In Vitro," J. Histochem. Cytochem., 2002, vol. 50, No. 12, pp. 1659-1662.

Henary, M.M. et al., "Zinc(II)-Selective Ratiometric Fluorescent Sensors Based on Inhibition of Excited-State Intramolecular Proton Transfer," Chem. Eur. J., 2004, vol. 10, pp. 3015-3025.

Hirano, T. et al., "Highly Zinc-Selective Fluorescent Sensor Molecules Suitable for Biological Applications," J. Am. Chem. Soc., Nov. 28, 2000, vol. 122, pp. 12399-12400.

Hogstrand, C. et al., "Zinc transporters and cancer: a potential role for ZIP7 as a hub for tyrosine kinase activation," Trends. Mol. Med., Mar. 2009, vol. 15, No. 3, pp. 101-111.

Ikeda, A. et al., "Novel Cavity Design Using Calix[n]arene Skeletons: Toward Molecular Recognition and Metal Binding," Chem. Rev., 1997, vol. 97, pp. 1713-1734.

Joseph, R. et al., "Experimental and Computational Studies of Selective Recognition of $Hg^{2+}$ by Amide Linked Lower Rim 1,3-Dibenzimidazole Derivative of Calix[4]arene: Species Characterization in Solution and that in the Isolated Complex, Including the Delineation of the Nanostructures," J. Org. Chem., Jul. 1, 2008, vol. 73, pp. 5745-5758.

Joseph, R. et al., "Lower Rim 1,3-Di{bis(2-picolyl)}amide Derivative of Calix[4]arene (L) as Ratiometric Primary Sensor toward $Ag^+$ and the Complex of $Ag^+$ as Secondary Sensor toward Cys: Experimental, Computational, and Microscopy Studies and Inhibit Logic Gate Properties of L," J. Org. Chem., Oct. 9, 2009, vol. 74, pp. 8181-8190.

Kim, J.S. et al., "Calixarene-Derived Fluorescent Probes," Chem. Rev., Aug. 21, 2007, vol. 107, pp. 3780-3799.

Kimura, E. et al., "Monitoring apoptosis with fluorescent $Zn^{2+}$- indicators," Sci. STKE, Mar. 9, 2004, vol. 223, pp. 1-8.

Kiyose, K. et al., "Development of a Ratiometric Fluorescent Zinc Ion Probe in Near-Infrared Region, Based on Tricarbocyanine Chromophore," J. Am. Chem. Soc., 2006, vol. 128, pp. 6548-6549.

Kumar, M. et al., "A reversible fluorescent $Hg^{2+}/K^+$ switch that works as keypad lock in the presence of F ion," Chem. Commun., Nov. 6, 2009, pp. 7384-7386.

Larson, A.A. et al., "Manipulations of Zinc in the Spinal Cord, by Intrathecal injection of Zinc Chloride, Disodium-Calcium-EDTA, or dipicolinic Acid, Alter Nociceptive Activity in Mice," J. Pharmacol. Exp. Ther., Sep. 1997, vol. 282, No. 3, pp. 1319-1325.

Leray, I. et al., "Calixarene-Based Fluorescent Molecular Sensors for Toxic Metals," Eur. J. Inorg. Chem., 2009, pp. 3525-3535.

Lim, N.C. et al., "DPA-substituted coumarins as chemosensors for zinc(II): modulation of the chemosensory characteristics by variation of the position of the chelate on the coumarin," Chem. Commun., Apr. 1, 2004, pp. 1094-1095.

Lim, N.C. et al., "Illuminating Zinc in Biological Systems," Chem. Eur. J., 2005, vol. 11, pp. 38-49.

Lukowiak, B. et al., "Identification and Purification of Functional Human Beta-cells by a New Specific Zinc-fluorescent Probe," J. Histochem. Cytochem., 2001, vol. 49, No. 4, pp. 519-527.

Masuoka, J. et al., "Zinc(II) and Copper(II) Binding to Serum Albumin; A comparative study of dog, bovine, and human albumin," J. Biolog. Chem., Oct. 14, 1994, vol. 269, No. 41, pp. 25557-25561.

Mothes, E. et al., "Evidence that the Principal $Co^{II}$-Binding Site in Human Serum Albumin is not at the N-Terminus: Implication on the Albumin Cobalt Binding Test for Detecting Myocardial ischemia," Biochemistry, Feb. 3, 2007, vol. 46, pp. 2267-2274.

Nolan, E.M. et al., "Small-Molecule Fluorescent Sensors for Investigating Zinc Metalloneurochemistry," ACC. Chem. Res., Jan. 2009, vol. 42, No. 1, pp. 193-203.

Ohyoshi, E. et al., "The interaction between human and bovine serum albumin and zinc studied by a competitive spectrophotometry," J. Inorg. Biochem., 1999, vol. 75, pp. 213-218.

Park, S.Y. et al., "A Pyrenyl-Appended Triazole-Based Calix[4]arene as a Fluorescent Sensor for $Cd^{2+}$ and $Zn^{2+}$," J. Org. Chem., Sep. 26, 2008, vol. 73, pp. 8212-8218.

Parkesh, R. et al., "Highly selective 4-amino-1,8-naphthalimide based fluorescent photoinduced electron transfer (PET) chemosensors for Zn(II) under physiological pH conditions," Org. Biomol. Chem., 2007, vol. 5, pp. 310-317.

Pathak, R.K. et al., "A lower rim triazole linked calix[4]arene conjugate as a fluorescence switch on sensor for $Zn^{2+}$ in blood serum milieu," Chem. Commun., 2010, vol. 46, pp. 4345-4347, [Supplementary Material] S1-S15.

Pathak, R.K. et al., "Selective recognition of $Zn^{2+}$ by salicylaldimine appended triazole-linked di-derivatives of calix[4]arene by enhanced fluorescence emission in aqueous-organic solutions: role of terminal -$CH_2OH$ moieties in conjunction with the imine in recognition," Tetrahedron Letters, 2009, vol. 50, pp. 2730-2734.

Prasad, A.S. et al., "Zinc and immunity," Mol. Cell. Biochem., 1998, vol. 188, pp. 63-69.

Prasad, A.S., "Zinc in Human Health: Effect of Zinc on Immune Cells," Mol. Med., 2008, vol. 14, pp. 353-357.

Qian, F. et al., "Visible Light Excitable $Zn^{2+}$ Fluorescent Sensor Derived from an Intramolecular Charge Transfer Fluorophore and Its in Vitro and in Vivo application," J. Am. Chem. Soc., 2009, vol. 131, pp. 1460-1468.

Que, E.L., "Metals in Neurobiology: Probing their chemistry and biology with molecular imaging," Chem. Rev., 2008, vol. 108, pp. 1517-1549.

Ren, J. et al., "Alpha-Lactalbumin Possesses a Distinct Zinc Binding Site," J. Biolog. Chem., Sep. 15, 1993, vol. 268, No. 26, pp. 19292-19298.

Rostovtsev, V.V. et al., "A Stepwise Huisgen Cycloaddition Process: Copper(I)-Catalyzed Regioselective 'Ligation' of Azides and Terminal Alkynes," Angew. Chem. Int. Ed., 2002, vol. 41, No. 14, pp. 2596-2599.

Ruedas-Rama, M.J. et al., "Azamacrocycle Activated Quantum Dot for Zinc Ion Detection," Anal. Chem., Oct. 8, 2008, vol. 80, No. 21, pp. 8260-8268.

Sadler, P.J. et al., "$^1$H and $^{113}$Cd NMR Investigations of $Cd^{2+}$ and $Zn^{2+}$ Binding Sites on Serum Albumin: Competition with $Ca^{2+}$, $Ni^{2+}$, $Cu^{2+}$, and $Zn^{2+}$," Inorg. Chem., 1996, vol. 35, pp. 4490-4496.

Senthilvelan, A. et al., "Cooperative Recognition of a Copper Cation and Anion by a Calix[4]arene Substituted at the Lower Rim by a Beta-Amino-Alpha,Beta-Unsaturated Ketone," Chem. Eur. J., May 15, 2009, vol. 15, pp. 6152-6160.

Shankar, A.H. et al., "Zinc and immune function: the biological basis of altered resistance to infection[1-3]," Am. J. Clin. Num., 1998, vol. 68(suppl), pp. 447S-463S.

Stewart, A.J. et al., "Interdomain zinc site on human albumin," Proc. Natl. Acad. Sci., Apr. 1, 2003, vol. 100, No. 7, pp. 3701-3706.

Tamanini, E. et al., "A Synthetically Simple, Click-Generated Cyclam-Based Zinc(II) Sensor," Inorg. Chem., 2009, vol. 48, No. 1, pp. 319-324.

Unob, F. et al., "An Anthracene-Based Fluorescent Sensor for Transition Metal Ions Derived from Calix[4]arene," Tetrahedron Letters, 1998, vol. 39, pp. 2951-2954.

Wang, J. et al., "A pH resistant Zn(II) sensor derived from 4-aminonaphthalimide: design, synthesis and intracellular applications," J. Mater. Chem., Mar. 14, 2005, vol. 15, pp. 2836-2839.

Wu, Y. et al., "Boron dipyrromethene fluorophore based fluorescence sensor for the selective imaging of Zn(II) in living cells," Org. Biomol. Chem., Mar. 16, 2005, vol. 3, pp. 1387-1392.

Yoruk, I. et al., "Serum concentration of Copper, Zinc, Iron, and Cobalt and the Copper/Zinc Ratio in Horses with Equine Herpesvirus-1," Biol. Trace Elem. Res., May 16, 2007, vol. 118, pp. 38-42.

CALIX[4]ARENES FOR THE SELECTIVE DETECTION OF ZN²⁺

FIELD

The present technology generally relates to ion detection.

BACKGROUND

Zinc is an essential nutrient and is necessary for the functioning of several metalloenzymes in humans and animals. Zinc deficiency is associated with anorexia, impaired immune, neural and reproductive functions. Zinc ions are present in neuronal cells. Due to its importance in human growth and development, human serum contains about 19 μM of this ion. Imbalanced homeostasis of $Zn^{2+}$ may cause a variety of diseases. However, an excess of zinc compounds such as oxides, sulfates, sulfides, and chlorides are known to cause problems in the respiratory tract and lead to bronchopneumonia and pneumonitis, developmental defects, inflammatory reactions, and even death. Prolonged oral exposure to zinc may also reduce copper absorption. Estimates of the minimal risk levels of zinc range from 77-600 mg/m³ for inhalation, and is 0.3 mg/kg/day for oral exposure. There is a need for compounds that can detect $Zn^{2+}$ and for methods for detecting $Zn^{2+}$, for example in blood serum. Provided herein are compounds and methods suitable for detecting $Zn^{2+}$ in a variety of samples.

SUMMARY

In one aspect, a compound of Formula I is provided:

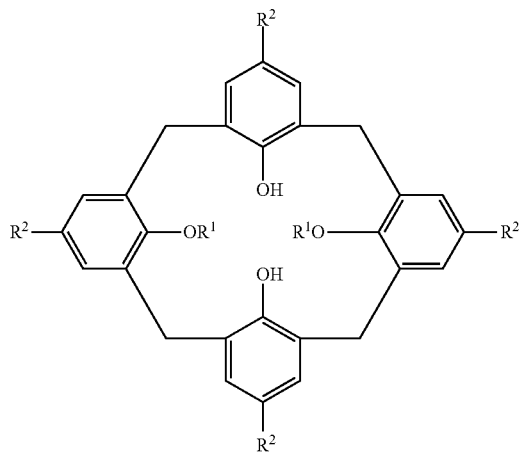

I or a salt thereof; wherein: each $R^1$ is a group of Formula:

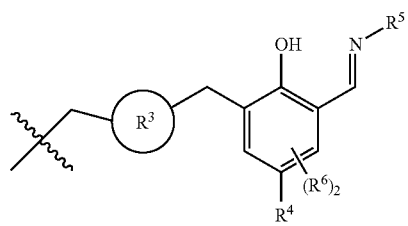

$R^2$ is H, $C_1$-$C_8$ alkyl, or $C_3$-$C_8$ cycloalkyl; $R^3$ is a 5-membered heteroaryl; $R^4$ is H or $C_1$-$C_8$ alkyl; $R^5$ is $C_1$-$C_8$ alkyl or $C_1$-$C_8$ cycloalkyl; and $R^6$ is H or $C_1$-$C_8$ alkyl. In one embodiment, $R^3$ is a divalent 1,2,3-triazole moiety.

In another aspect, a complex is provided including the compound of Formula I and a $Zn^{2+}$ ion. In another aspect, a method of determining the presence or absence of $Zn^{2+}$ in a solution is provided. This method includes contacting the compound of Formula I with a test sample to form a solution; and recording a fluorescence spectrum of the solution, wherein in the presence of $Zn^{2+}$, the solution exhibits fluorescence intensity at about 450 nm that is greater than a fluorescence intensity of a solution that does not contain $Zn^{2+}$. In one embodiment, the presence of $Zn^{2+}$ can be determined in the presence of other metal ions in the sample.

In another aspect, a method of synthesizing the compound of Formula I is provided which includes contacting a compound of Formula II:

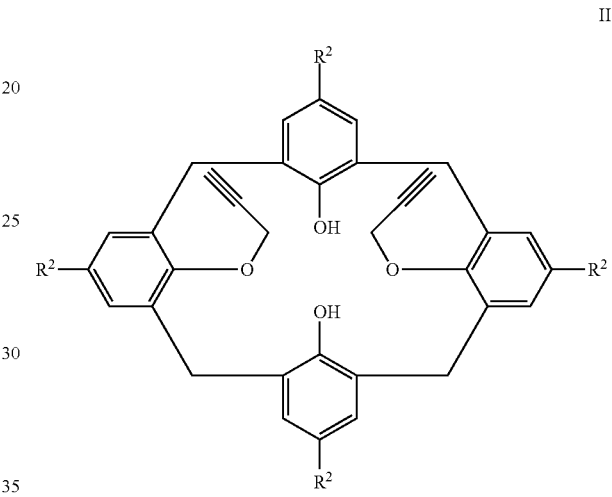

II with a compound of Formula III:

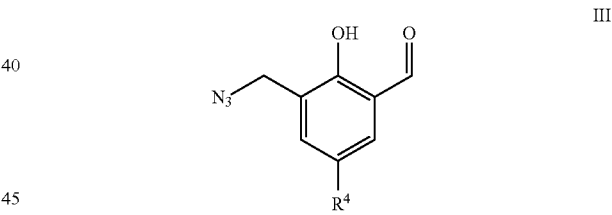

III to provide a compound of Formula IV:

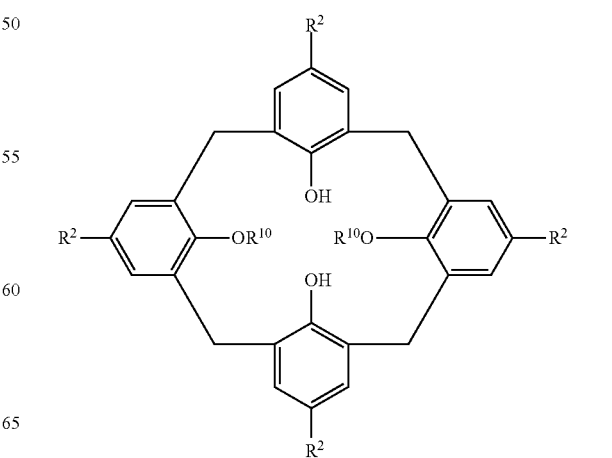

IV or a salt thereof, wherein $R^{10}$ is:

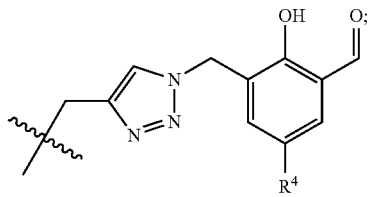

$R^2$ is H, $C_1$-$C_8$ alkyl or $C_3$-$C_8$ cycloalkyl; and $R^4$ is H or $C_1$-$C_8$ alkyl.

In one embodiment, the method also includes contacting the compound of Formula IV with $R^5NH_2$, or a salt thereof, to provide a compound of Formula I:

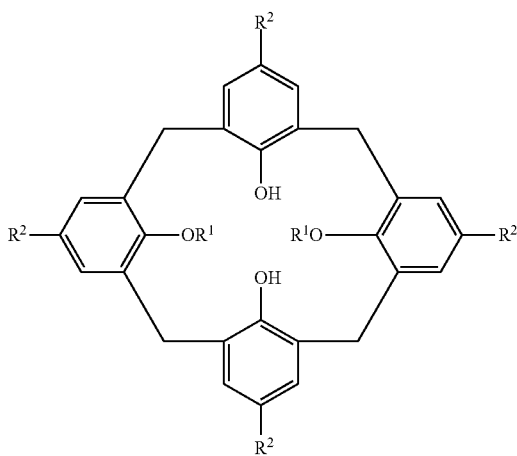

Wherein: $R^1$ is

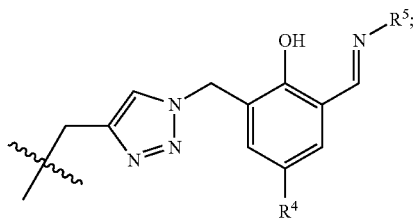

and $R^5$ is $C_1$-$C_8$ alkyl or $C_1$-$C_8$ cycloalkyl.

BRIEF DESCRIPTION OF THE DRAWINGS

In FIG. 4, the symbols correspond to:
○=$Zn^{2+}$, ●=$Li^+$, ▲=$Na^+$, ▼=$K^+$, ◄=$Cs^+$, ►=$Mg^{2+}$,
◆=$Ca^{2+}$, =$Sr^{2+}$, =$Ba^{2+}$, ★=$Mn^{2+}$ =$Fe^{2+}$,
=$Co^{2+}$, =$Ni^{2+}$, =$Cu^{2+}$, =$Cd^{2+}$,
=$Hg^{2+}$, =$Ag^+$.

DETAILED DESCRIPTION

Figure 1A:
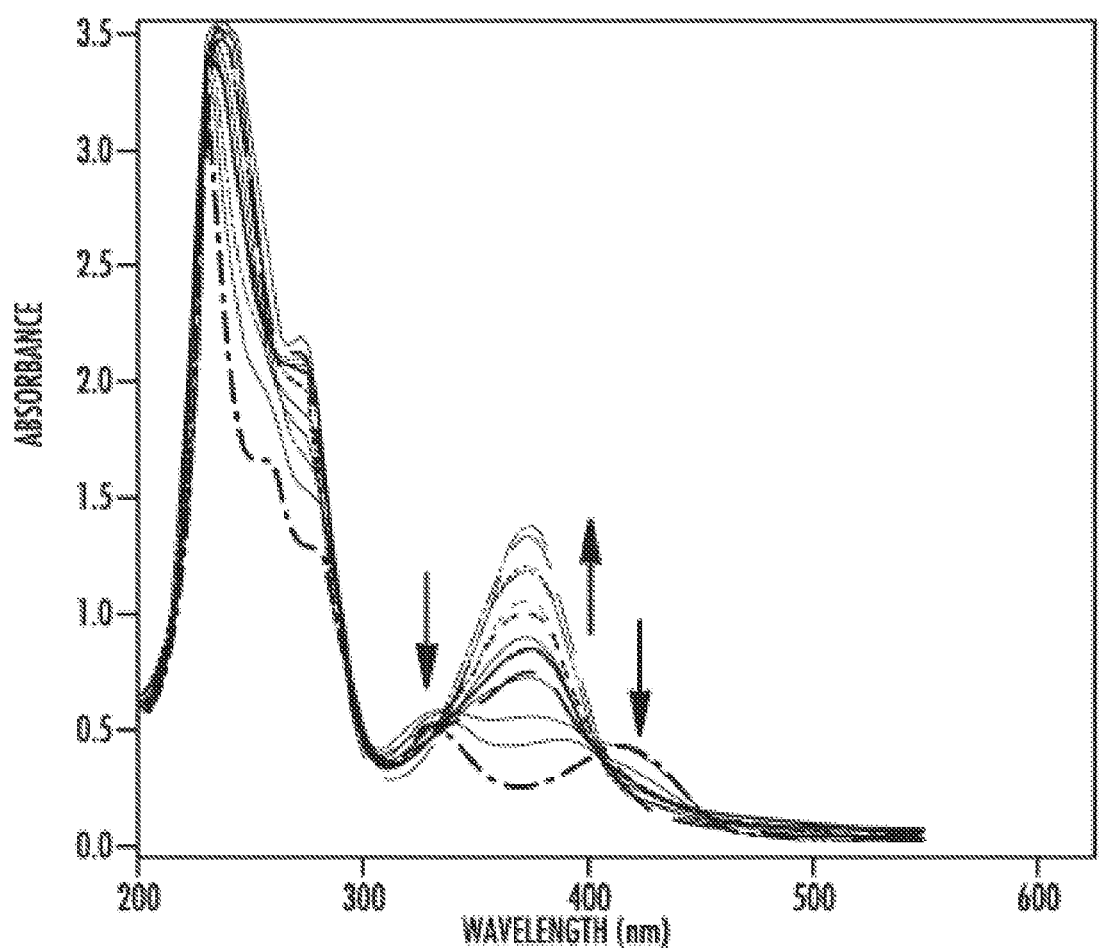
FIG. 1A is an absorption spectra of the titration of the compound L, with $Zn^{2+}$ in aqueous methanolic (1:4 v/v) HEPES buffer (pH ~7.4)

In the following detailed description, the illustrative embodiments described are not meant to be limiting. Other embodiments may be utilized, and other changes may be made, without departing from the spirit or scope of the subject matter presented here.

As used herein, unless otherwise stated, the singular forms "a," "an," and "the" include plural reference.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Provided herein are calix[4]arene compounds, their complexes with $Zn^{2+}$ ion, methods of making these compound and complexes, and methods of determining the presence and absence of $Zn^{2+}$ ion in an analyte. Thus, in one aspect, a compound of Formula I is provided:

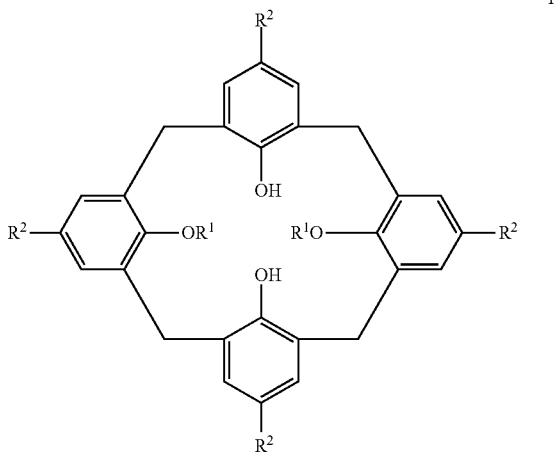

or a salt thereof; wherein: each $R^1$ is a group of Formula:

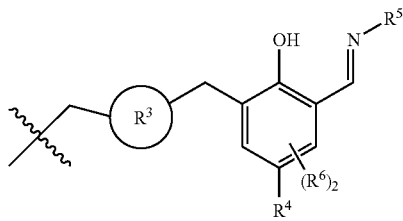

$R^2$ is H, $C_1$-$C_8$ alkyl, or $C_3$-$C_8$ cycloalkyl; $R^3$ is a 5-membered heteroaryl; $R^4$ is H or $C_1$-$C_8$ alkyl; $R^5$ is $C_1$-$C_8$ alkyl or $C_1$-$C_8$ cycloalkyl; and $R^6$ is H or $C_1$-$C_8$ alkyl.

In one embodiment, $R^3$ is a divalent 1, 2, 3-triazole moiety. In another embodiment, $R^1$ is of Formula:

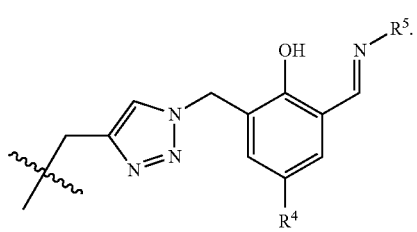

In another embodiment, $R^2$ is methyl, ethyl, propyl, isopropyl, n-butyl, tert-butyl, amyl, octyl, cyclopropyl, cyclobutyl, cyclopentyl or cyclohexyl. In another embodiment, $R^2$ is tert-butyl. In another embodiment, $R^4$ is H, methyl, ethyl, propyl, isopropyl, n-butyl, tert-butyl, amyl, octyl, cyclopropyl, cyclobutyl, cyclopentyl or cyclohexyl. In another embodiment, $R^4$ is tert-butyl. In another embodiment, $R^5$ is methyl, ethyl, propyl, n-butyl, or tert-butyl. In another embodiment, $R^5$ is butyl. In another embodiment, $R^6$ is H. In another embodiment, $R^2$ is tert-butyl and $R^1$ is a group of Formula:

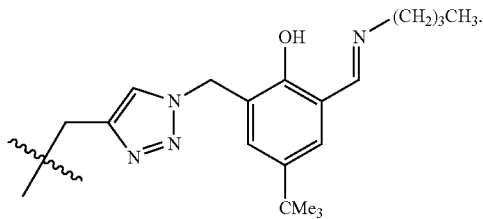

The above compounds may form salts with inorganic or organic acids or bases. In one embodiment, the salts include the phenoxide salts of compounds of Formula I. In another embodiment, the phenoxide moiety is part of the salicylaldimine or the $R^1$ moiety. In the phenoxide salts, the cation may be a variety of organic and inorganic cations. In one embodiment, the cation is a $Zn^{2+}$ cation. Salts may also include, without limitation, acid salts, formed with acids such of $HClO_4$, $HCl$, $H_2SO_4$, and $H_3PO_4$, as well as acetic acid or trifluoroacetic acid.

In another aspect, a $Zn^{2+}$ salt or a $Zn^{2+}$ complex of the compound of Formula I and a $Zn^{2+}$ ion is provided. In certain embodiments, the $Zn^{2+}$ ion in the $Zn^{2+}$ complex is bonded to the salicylaldimine moiety via imino nitrogens and phenoxide oxygens.

In another aspect, a method of synthesis of the compound of Formula I is provided including contacting a compound of Formula II:

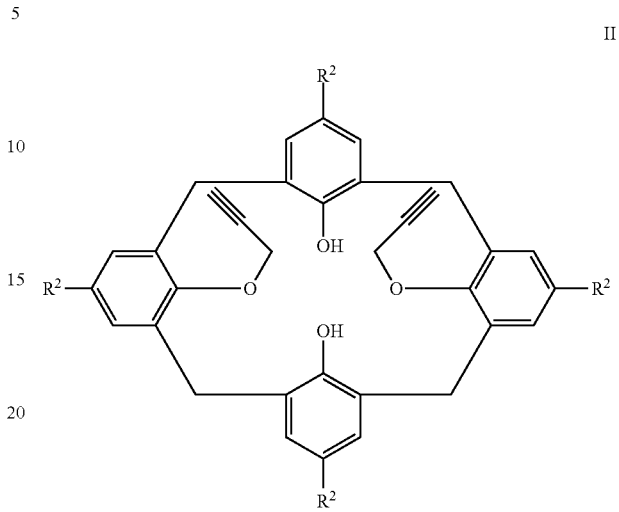

with a compound of Formula III:

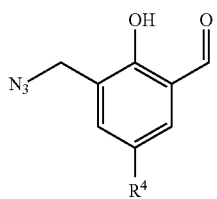

to provide a compound of Formula IV:

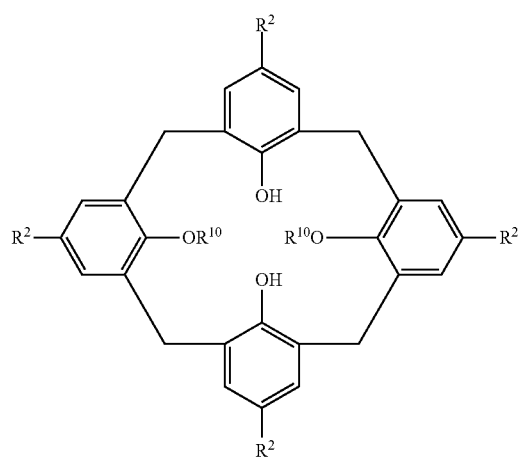

or a salt thereof, wherein $R^{10}$ is:

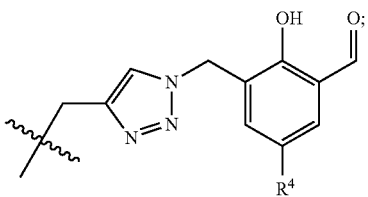

$R^2$ is H, $C_1$-$C_8$ alkyl or $C_3$-$C_8$ cycloalkyl; and $R^4$ is H or $C_1$-$C_8$ alkyl. In one embodiment, compounds of Formula II and Formula III are contacted in the presence of $Cu^{2+}$. In a more specific embodiment, compounds of Formula II and Formula III are contacted in the presence of $CuSO_4 \cdot 5H_2O$ and sodium ascorbate in dichloromethane/water.

In one embodiment, the method also includes contacting the compound of Formula IV with $R^5$—$NH_2$, or a salt thereof, to provide a compound of Formula I:

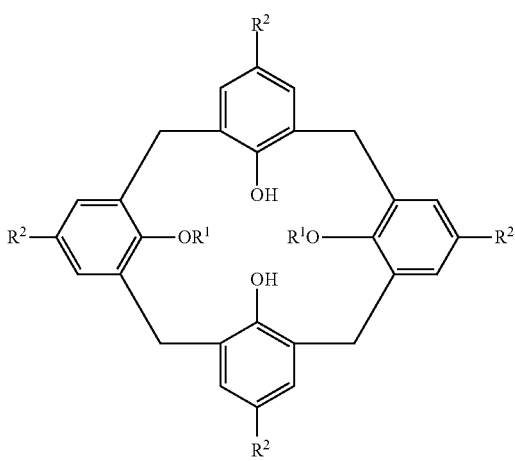

wherein: $R^1$ is

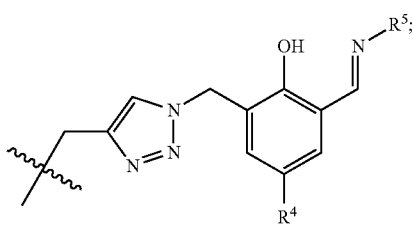

and $R^5$ is $C_1$-$C_8$ alkyl or $C_1$-$C_8$ cycloalkyl. In another embodiment, $R^2$ and $R^4$ are tert-butyl, and $R^5$ is n-butyl.

In another embodiment, the method also includes contacting a compound of Formula I with a zinc salt to provide the zinc complexes. A variety of zinc salts may thus be employed including, without limitation, various zinc carboxylates. In another embodiment, the zinc carboxylate is zinc acetate.

In various other embodiments, $R^1$, $R^2$, $R^3$, $R^4$, and $R^5$ are defined as in any aspect or embodiment hereinabove. A skilled artisan will appreciate that the contacting may be performed in a variety of solvents including, without limitation, chlorinated solvents, dimethylformamide (DMF), ketones, alcohols, and water. After reacting, the product may be separated from the reaction mixture, for example, following an aqueous work-up. The product may be separated from other impurities by a variety of methods, including, without limitation, distillation, precipitation, crystallization, and chromatographic separation.

In another aspect, a method of determining the presence or absence of $Zn^{2+}$ in a solution is provided. The method may be qualitative (measuring the presence or absence of $Zn^{2+}$) or quantitative (measuring the concentration of $Zn^{2+}$). Such methods include contacting the compound of Formula I with a test sample to form a solution; and recording a fluorescence spectrum of the solution. The presence of $Zn^{2+}$ in the solution is confirmed by the exhibition of fluorescence intensity at about 450 nm that is greater than a fluorescence intensity of a solution or sample that does not contain $Zn^{2+}$. The method may further comprise contacting the compound of Formula I with a blank sample lacking $Zn^{2+}$ to form a blank solution, and recording the fluorescence spectrum of the blank solution. In other words, any signal at 450 nm is enhanced in the presence of the $Zn^{2+}$, or if no signal is present, the signal appears in the presence of $Zn^{2+}$. For example, the enhancement at about 450 nm that is greater than a fluorescence intensity of a solution that does not contain $Zn^{2+}$, may be from about 2 to 50, about 4 to 25, or about 8 to 10 fold greater.

In another embodiment, the test sample includes serum. In another embodiment, the test sample includes soil, water or food. In another embodiment, the test sample is one of biological origin. For example, samples of biological origin may include, but are not limited to blood, urine, cells, and/or tissue.

A wavelength of 450 nm may be used, or alternatively, a wavelength of about 450 nm may be used. As used herein, about 450 nm includes, from 400 nm to 525 nm, from 425 nm to 500 nm, from 450 nm to 475 nm, and 450 nm. The fluorescence spectrum is recorded using a an excitation wavelength ($\lambda_{ex}$) from 360 nm to 400 nm, or from 370 nm to 390 nm, or which is about 380 nm.

The test sample may include aqueous methanolic (4-(2-hydroxyethyl)-1-piperazineethanesulfonic acid (HEPES) buffer. Test samples may generally have any pH value. For example, $Zn^{2+}$ ions may be determined in test samples having a pH of 6, 7, 8, 9, 10, or 11, or from 6 to 11, 7 to 10, or from 8 to 9. Biological samples typically have pH values of about 7.

In some embodiments, the compound of Formula I and the test sample can both be dissolved in the same solvent or different solvents prior to the fluorescence testing. Alternatively, the compound of Formula I can be added without a solvent. The solvent can be a pure solvent or a mixture of solvents. If the solvents are different, they typically will be miscible with each other. For example, the compound of Formula I and the test sample can be dissolved in solvents which may include water, alcohol, or acetonitrile. In some embodiments, the test sample and/or the control sample includes an aqueous solution. In some embodiments, the test sample may be prepared by dissolving the sample to be analyzed in an aqueous solution including water in combination with water-miscible solvents. In some embodiments, the sample to be analyzed is dissolved in an aqueous solution that includes acetonitrile or methanol. In some embodiments, the sample to be analyzed is dissolved in a solution including aqueous methanol. In some embodiments, the aqueous methanol solution includes about 10% to about 90% methanol (by volume). In other embodiments, the aqueous sample solution includes about 40% to about 75% acetonitrile (by volume) or about 50% acetonitrile (by volume).

The methods provided herein can have very good sensitivity down to the part per billion (ppb) levels. In another embodiment, the presence of $Zn^{2+}$ ions may be detected, at a concentration of at least 20 ppb, at least 100 ppb, at least 200 ppb, at least 300 ppb, at least 500 ppb, or at least 1 part per million (ppm). In other embodiments, the $Zn^{2+}$ may be detected from about 20 ppb to about 10 ppm, from about 25 ppb to about 1 ppm, from about 30 ppb to about 500 ppb, or from about 30 ppb to about 100 ppb.

The methods provided are very sensitive for the presence of $Zn^{2+}$, even in the presence of one or more other metal ions. Thus, in another embodiment, the compounds of Formula I may detect $Zn^{2+}$ in the presence of various other ions. Other metal ions may include, but are not limited to, divalent or trivalent metal ions. In another embodiment, the divalent metal ion is an alkaline earth metal ion, including without limitation, $Mg^{2+}$, $Ca^{2+}$ $Sr^{2+}$, $Ba^{2+}$, $Mn^{2+}$, $Fe^{2+}$, $Co^{2+}$, $Ni^{2+}$, $Cu^{2+}$, $Hg^{2+}$ or $Cd^{2+}$.

In another embodiment, the other metal ion is a monovalent metal ion. For example, monovalent metal ions may include, but are not limited to $Li^+$, $Na^+$, $K^+$, $Cs^+$, or $Ag^+$. In another embodiment, the presence of $Zn^{2+}$ may be determined in the presence of $Hg^{2+}$, $Cd^{2+}$, $Li^+$, $Na^+$, $K^+$, $Cs^+$, $Mg^{2+}$, $Ca^{2+}$ $Sr^{2+}$, $Ba^{2+}$, $Mn^{2+}$, $Fe^{2+}$, $Co^{2+}$, $Ni^{2+}$, $Co^{2+}$, or $Ag^+$ ion. In one embodiment, a 100 ppb to 500 ppb range concentration of $Zn^{2+}$ ions can be detected in the presence of about 6.5 ppm concentration of $Hg^{2+}$ and about 6.5 ppm concentration of $Cd^{2+}$.

The compounds of Formula I may detect $Zn^{2+}$ in the presence of blood serum and of various albumins that are known to form complexes with $Zn^{2+}$. Thus, the presence of $Zn^{2+}$ may be determined in the presence of HSA, BSA, or LA. In another embodiment, the albumin is present in the test solution at a concentration of about 1 mg/mL of proteins. The $Zn^{2+}$ may also be detected in blood serum, at concentrations of about 300 ppb, 400 ppb, 500 ppb, 1 ppm, or from 100 ppb to 1 ppm.

As used herein, "alkyl" groups are monovalent hydrocarbon radicals and include straight chain and branched alkyl groups having from 1 to about 20 carbon atoms, and alternatively from 1 to 12 carbons or, in some embodiments, from 1 to 8 carbon atoms. Examples of straight chain alkyl groups include without limitation methyl, ethyl, n-propyl, n-butyl, n-pentyl, n-hexyl, n-heptyl, and n-octyl groups. Examples of branched alkyl groups include, without limitation, isopropyl, sec-butyl, t-butyl, neopentyl, and isopentyl groups. Alkyl groups may be unsubstituted or substituted. Representative substituted alkyl groups may be substituted one or more times with, for example, amino, carboxyl, thio, hydroxy, cyano, alkoxy, phenyl, and/or F, Cl, Br, and I groups.

As used herein, "alkoxy" refers to an —O-alkyl moiety. Examples of alkoxy groups include, without limitation, methoxy, ethoxy, isopropoxy, and benzyloxy.

As used herein, "cycloalkyl" groups are monovalent cyclic hydrocarbons. Examples of cyloalkyl groups include, without limitation, cyclopropyl, cyclobutyl, cyclopentyl, and cyclohexyl. Cycloalkyl groups may be unsubstituted or substituted.

As used herein, "5-membered heteroaryl" refers to a cyclic aromatic ring containing 5 ring atoms and containing at least 1, and up to 4, heteroatoms selected from N, O, and S. Such 5 membered heteroaryl groups may be unsubstituted or substituted. Examples of 5 membered heteroaryls include, without limitation, diazoles, furan, imidazole, oxadiazole, pyrrole, thiadiazole, thiophene, triazoles, and the like.

As used herein, "substituted amino" refers to —NHRx or —N($R^x$)$_2$ wherein each Rx independently is alkyl, —CO-alkyl, $CO_2$-alkyl, $SO_2$-alkyl, or two Rx groups together with the nitrogen atom to which they are bonded for a cyclic ring.

The present technology, thus generally described, will be understood more readily by reference to the following example, which is provided by way of illustration and is not intended to limit the present technology.

EXAMPLES

Example 1

Overall Synthetic Scheme. L, a compound of Formula I, its precursors, and control compounds used to test the superior $Zn^{2+}$ detectability of L, were synthesized as shown in Scheme 1. To incorporate binding motifs and a fluorophore on the calix[4]arene platform, a triazole moiety was used as a linker. An aldehyde precursor, $L_3$, was synthesized by reacting calix [4]arene based di-propargyl ether derivative ($L_1$) with the substituted salicylaldehyde azide derivative ($L_2$) through a click reaction as shown in Scheme 1. The receptor molecule (L) was synthesized in quantitative yield by the condensing $L_3$ with n-butyl amine in methanol (Scheme 1).

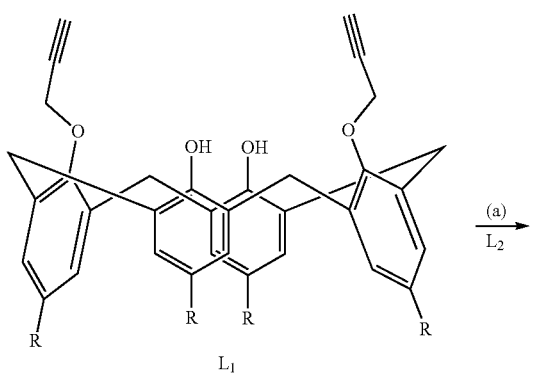

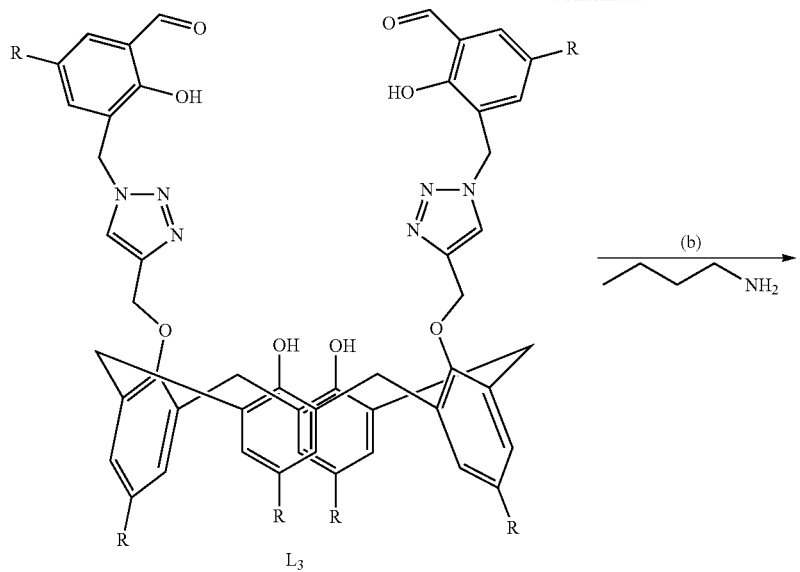
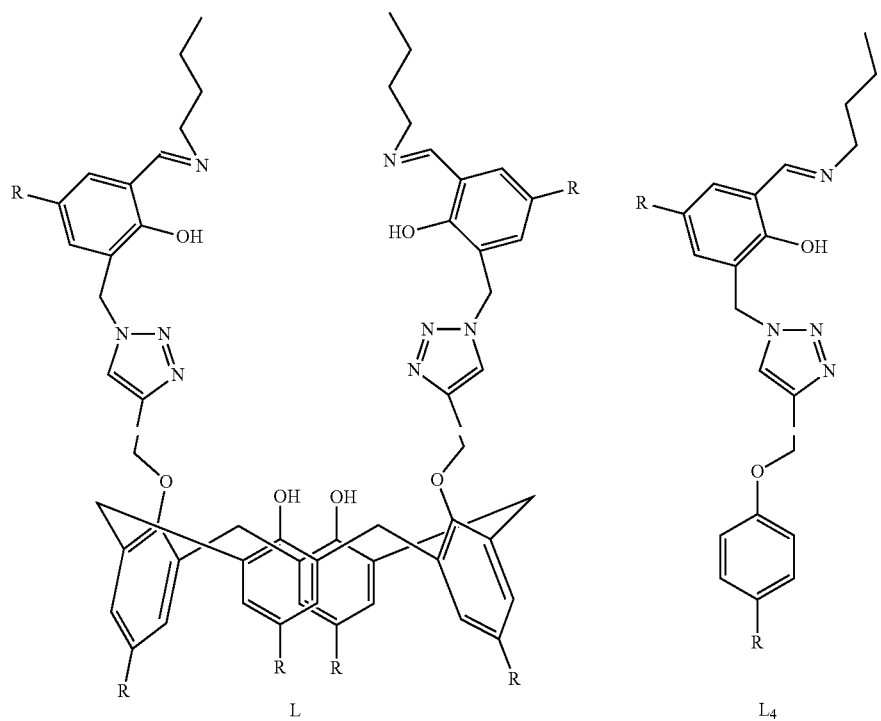
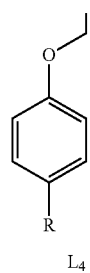

Scheme 1. Synthesis of L and its control molecules: (5) 5-tert-butyl-3-(azidomethyl)-2-hydroxybenzaldehyde ($L_2$), $CuSO_4 \cdot 5H_2O$ and sodium ascorbate in dichloromethane:water (1:1), rt, 12 hr; (b) n-butylamine, methanol, room temperature, 4, hours. R=tert-butyl.

Example 1A

Synthesis of $L_1$. $L_1$, a compound of Formula II, was synthesized as follows. A mixture of potassium carbonate (5.10 g, 36.72 mmol), p-tert-butylcalix[4]arene (10 g, 15.43 mmol) in acetone (200 mL) was stirred at room temperature for 1 hour. A solution of propyn-2-yl-4-methylbenzenesulfonate (6.49 g, 30.80 mmol) in acetone (50 mL) was added dropwise into the stirred mixture over 30 minutes. The reaction mixture was refluxed for 48 hours and was then allowed to cool to room temperature. The reaction mixture was filtered over Celite to remove insoluble particles and the filtrate was concentrated under vacuum. Hydrochloric acid (100 mL, 2 M) was added to the concentrated reaction mixture and the product was extracted with dichloromethane (3×100 mL). The combined organic extracts were then successively washed with water and brine (100 mL), dried over anhydrous $Na_2SO_4$, filtered, and evaporated to dryness under vacuum. The crude product was recrystallized from $CH_2Cl_2/CH_3OH$ to afford $L_1$ as a white solid (9.10 g, 82% yield). $^1H$ NMR (400 MHz, $CDCl_3$) (ppm): 7.07 (s, 4H, Ar—H), 6.73 (s, 4H, Ar—H), 6.50 (s, 2H, OH), 4.74 (d, J=2.4 Hz, 4H, $OCH_2$), 4.37 (d, J=13.4 Hz, 4H, $ArCH_2Ar$), 3.33 (d, J=13.4 Hz, 4H, $ArCH_2Ar$), 2.54 (t, J=2.4 Hz, 2H, CCH), 1.30 (s, 18H, $(CH_3)_3$), 0.90 (s, 18H, $(CH_3)_3$).

Example 1B

Synthesis of $L_2$. $L_2$, a compound of Formula III, was synthesized starting with p-t-butyl phenol, and via the intermediacy of compounds 1 and 2, as shown in Scheme 2.

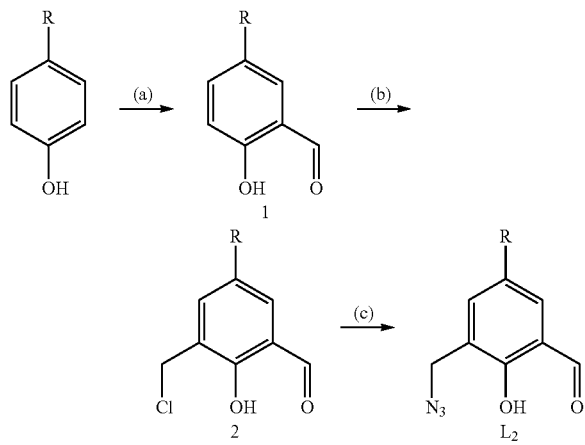

Scheme 2. Synthesis of 5-tert-butyl-3-(azidomethyl)-2-hydroxybenzaldehyde (a) $SnCl_4$, $Bu_3N$, $(CH_2O)_n$, dry toluene, reflux; (b) 37% formaldehyde, conc. HCl, rt for 24 hours, and (c) $NaN_3$, $CH_3CN$, rt, 12 hours.

Compound 2 (2.65 g, 11.89 mmol) was added to a solution of sodium azide (1.519 g, 23.37 mmol) in dimethylformamide (30 mL) under stirring for 12 hours. After completion of reaction mixture was diluted with water and ethylacetate (100 mL). The organic layer was separated and washed with water and brine. $L_2$, a yellow liquid, was obtained upon evaporating the organic solvent. Yield 89% $^1H$ NMR ($CDCl_3$, 400 Hz) 11.2 (broad s, H, Sal-OH), 9.99 (s, H, CHO—H), 7.55 (dd, 1H, Sal-H), 7.59 (s, 1H, Ar—H), 4.48 (s, 2H, Sal-$CH_2$), 1.35 (s, 9H, Ar—$(CH_3)_3$). IR: $v_{max}$=3471, 2961, 2686, 2104, 1676.

Example 1C

Synthesis of $L_3$. $L_3$, a compound of formula IV, was synthesized as follows. $L_1$ (3.0 g, 4.14 mmol) was added to the solution of $L_2$ (2.12 g, 9.53 mmol) in dichloromethane (100 mL) and water (50:50) mixture. To this solution was added $CuSO_4 \cdot 5H_2O$ (124.04 g, 0.50 mmol) and sodium ascorbate (328.0 mg, 1.70 mmol). The resulting solution was stirred for 12 hours at room temperature. Upon completion of the reaction as determined by TLC, the organic layer was separated and the aqueous layer was extracted with dichloromethane (2×50 mL). The combined organic layer was washed water and with brine (2×100 mL), dried over anhydrous $Na_2SO_4$, and the solvent was removed under vacuum. The crude product was purified by triturating with hexane followed by filtering the precipitate to provide $L_3$. Yield, 89.91%. $^1H$ NMR ($CDCl_3$, 400 MHz) δ(ppm): 11.30 (s, 2H, Sal-OH), 9.83 (s, 2H, sal-CHO), 8.08 (s, 2H, triazole-H), 7.62 (s, 2H, Sal-H) 7.49 (d, 2H, Sal-H), 7.15 (s, 2H, Ar—OH), 6.98 (s, 4H, Ar—H), 6.77 (s, 4H, Ar—H), 5.56 (s, 2H, Sal-$CH_2$), 5.18 (s, 2H, Ar—O—$CH_2$), 4.14 (d, J=13.0 Hz, 4H, $ArCH_2Ar$), 3.17 (d, J=13.0 Hz, 4H, $ArCH_2Ar$), 1.27 (s, 18H, Ar—$(CH_3)_3$), 1.26 (s, 18H, Ar—$(CH_3)_3$), 0.96 (Sal-$(CH_3)_3$). $^{13}C$ NMR ($CDCl_3$, 100 MHz) δ (ppm): 196.6, 157.1, 150.4, 149.6, 147.2, 144.2, 143.2, 141.5, 135.3, 132.6, 130.7, 127.8, 125.6, 125.0, 124.2, 123.1, 120.2, 69.8, 48.2, 34.2, 33.9, 33.8, 31.7, 31.2, 31.1, 31.02. IR:v=3463, 2959, 1656, 1483, $cm^{-1}$. EA calcd. for $C_{74}H_{90}N_6O_8$: C, 74.59; H, 7.61; N, 7.05. Found: C, 73.47; H, 7.24; N, 7.12 m/z (ES/MS) 1199.50 ([M]$^+$ 100%).

Example 1D

Synthesis of L. L, a compound of Formula I, was synthesized as follows. A mixture of $L_3$ (200 mg, 0.167 mmol) and butylamine (24.56 mg, 0.34 mmol) in methanol was stirred for 4 hours. Then the reaction mixture was heated at 60° C. for 1 hour to give clear yellow solution. The solvent was removed under vacuum to get a solid yellow product, which was recrystallized using methanol to provide L. Yield 95%. $^1H$ NMR ($CDCl_3$, 400 Hz) 14.11 (broad s, 2H, Sal-OH), 8.27 (s, 2H, imine-H), 8.07 (s, 2H, triazole-H), 7.40 (d, Sal-H) 7.20 (d, Sal-H) 7.10 (s, 2H, Ar—OH), 6.96 (s, 4H, Ar—H), 6.74 (s, 4H, Ar—H), 5.58 (s, 4H, Sal-$CH_2$), 5.1 (s, 4H, Ar—$OCH_2$), 4.14 (d, 4H, Ar—$CH_2$—Ar), 3.52 (t, 4H, N—$CH_2$), 3.28 (d, 4H, Ar—$CH_2$—Ar), 1.62 (quintet, N—$CH_2$—$CH_2$), 1.36 (Sextet, 4H, N—$CH_2CH_2$*$CH_2CH_3$), 1.26 (s, 18H, $(CH_3)_3$), 1.25 (s, 18H, $(CH_3)_3$), 0.94 (s, 18H, Sal-$(CH_3)_3$) 0.93 (t, 6H, N—$CH_2$—$CH_2$—$CH_2$—$CH_3$). $^{13}C$ NMR ($CDCl_3$, 200 Hz) δ (ppm): 164.7, 158.1, 150.6, 149.8, 147.0, 144.0, 141.5, 141.2, 133.0, 130.6, 128.5, 128.0, 126.0, 125.0, 124.2, 123.0, 118.2, 69.8, 58.9, 48.9, 34.1, 34.0, 33.9, 32.9, 31.9, 31.5, 31.1, 29.8, 20.4, 13.9. IR:v=3442, 2958, 1635, 1482, $cm^{-1}$. EA calcd. for $C_{82}H_{108}N_8O_6$: C, 75.66; H, 8.36; N, 8.61; O, 7.37. Found: C, 74.33; H, 8.22; N, 8.83 m/z (ES/MS) 1301.80 [M]$^+$ 100%).

Example 1E

Synthesis of a Zn complex of compound L, L-Zn. To a solution of L (0.167 mmol) in $CH_3CN$ (6 mL) was added a methanolic solution of $Zn(CH_3COO)_2 \cdot 2H_2O$ (0.175 mmol) and refluxed for 5 hours. After concentrating this solution, a light yellow precipitate formed, which was filtered, washed with cold MeOH, and dried under vacuum to give the desired product, L-Z complex. $\nu_{max}$ (KBr)/cm-1: 2958, 1621, 1547, 1483, 1461. 1H NMR (CDCl$_3$, 400 MHz): 8.69 (s, 2H, imine-H), 7.87 (s, 2H, triazole-H), 7.53 (d, Sal-H) 7.45 (s, 2H, Ar—OH) 7.02 (d, Sal-H), 7.02-6.74 (t, 8H, Ar—H), 5.84-5.80 (dd, 4H, Sal-CH$_2$), 5.20 (s, 4H, Ar—OCH$_2$), 4.19-3.76-3.25-2.67 (4d, 4H, Ar—CH$_2$—Ar), 3.34 (t, 4H, N—CH$_2$), 1.46 (quintet, N—CH$_2$—CH$_2$), 1.36 (Sextet, 4H, N—CH$_2$CH$_2$*CH$_2$CH$_3$), 1.30 (s, 18H, (CH$_3$)$_3$), 1.26 (s, 18H, (CH$_3$)$_3$), 0.99 (s, 18H, Sal-(CH$_3$)$_3$) 0.76 (t, 6H, N—CH$_2$—CH$_2$—CH$_2$—CH$_3$). $^{13}$C NMR (CDCl$_3$, 200 Hz) δ (ppm): 171.5, 166.3, 150.4, 149.2, 148.0, 144.2, 142.5, 137.4, 134.0, 133.5, 133.2, 133.0, 128.5, 128.3, 128.17, 126.1, 125.6, 125.4, 117.7, 70.3, 61.2, 50.5, 34.4, 34.3, 34.2, 32.8, 32.1, 31.8, 31.4, 20.4, 14.0, (ES/MS) 1403 [M]++K+(100). EA calcd. For C$_{74}$H$_{92}$N$_8$O$_{10}$: C, 70.90; H, 7.40; N, 8.94. Found: C, 66.88; H, 7.35; N, 8.87.

Example 2A

Mass, NMR and UV-absorption spectroscopy confirming the zinc-complexation. The formation of a 1:1 complex between Zn$^{2+}$ and L was also confirmed by the m/z=1403.8 (100%, [L+Zn$^+$ K–H+]), 1388.9 (85-90%, [L+Zn$^+$ Na]), and 1365.9 (35-45%, [L+Zn]) peaks observed in (electrospray ionization mass spectroscopy) ESI MS, where the isotopic distribution demonstrated the characteristic signature of zinc in each of these peaks. The complex was also confirmed by comparing the $^1$H NMR spectrum of L-Zn complex with that of L, where some resonances were shifted to down field and some to upfield, indicating a complex formation.

Figure 1B:
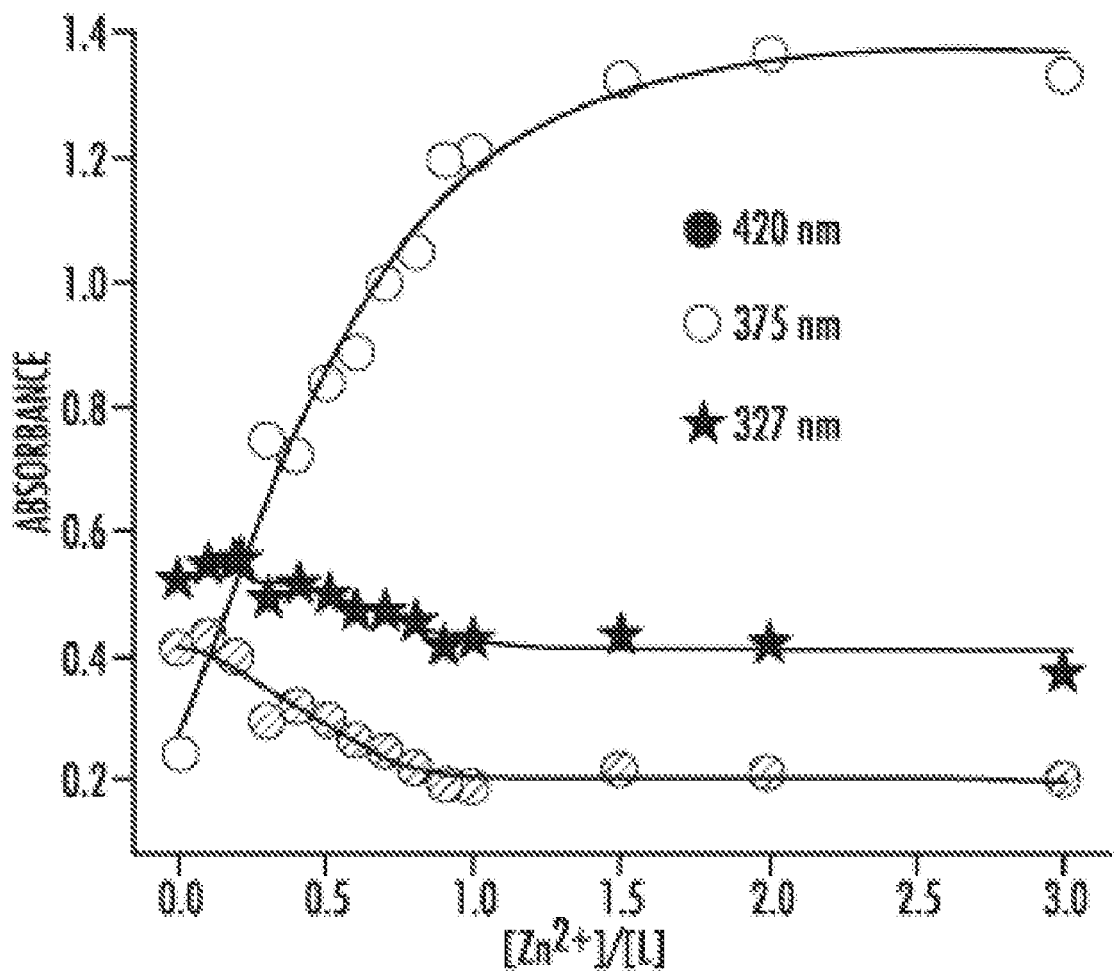
FIG. 1B is plots of absorbance v. $[Zn^{2+}]/[L]$ for different bands, according to Example 1.
Figure 2:
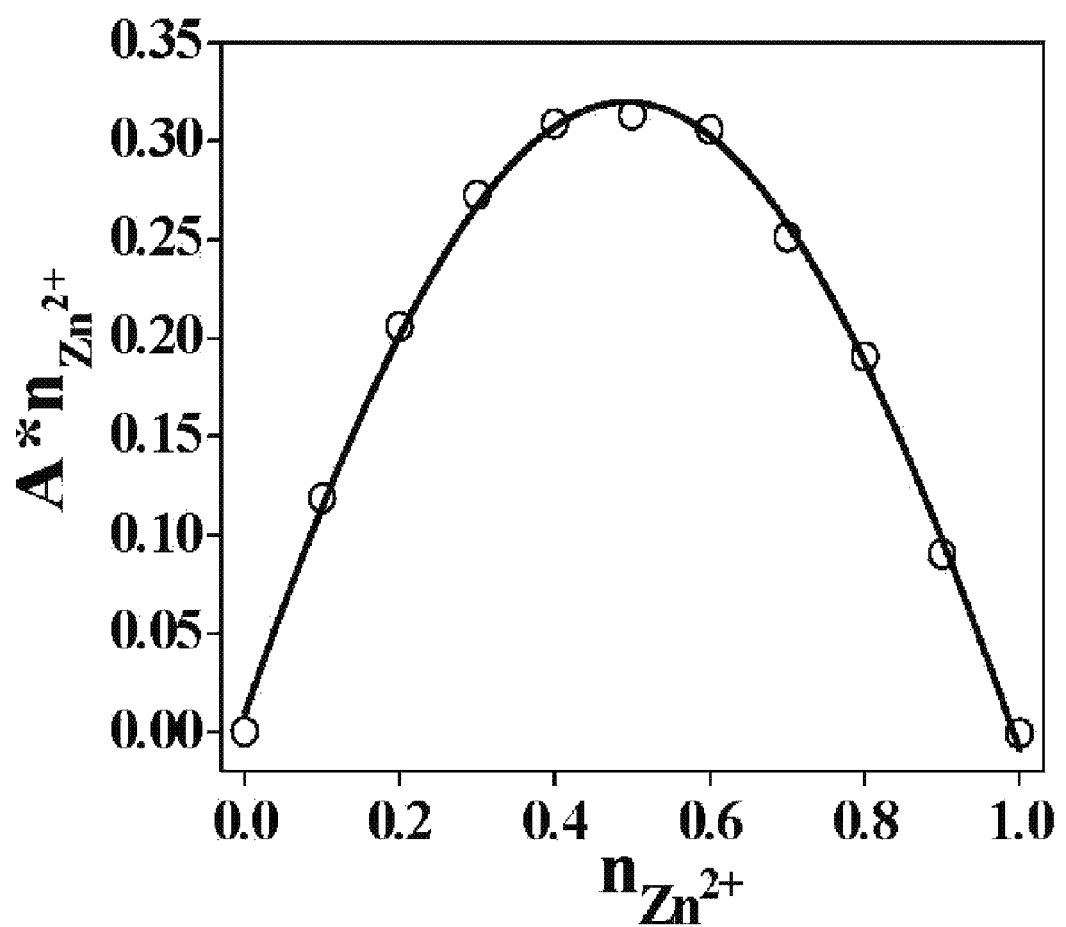
FIG. 2 is a plot of $n_m$ v. $An_m$, where $n_m$ is the mole fraction of $Zn^{2+}$ added and A is the corresponding absorbance, according to Example 1.

The absorption titration carried out between L and Zn$^{2+}$ in the same medium (FIG. 1A) exhibited three isosbestic points at 290, 335, and 405 nm indicating a transition between the unbound L and that of Zn$^{2+}$ bound L. L binds Zn$^{2+}$ via its two phenolic-oxygens and two imine nitrogens to form tetracordinated complex. The spectra also exhibited increase in absorbance in the about 375 nm bands and decrease in absorbance in case of about 320 and about 420 nm bands (FIG. 1B). The stoichiometry of the complex formed between L and Zn$^{2+}$ has been derived to be 1:1 based on Job's plot (FIG. 2).

Example 2B

Crystallization and structure determination of the zinc complex of L, Zn-L. X-ray diffraction quality crystals of the Zn-L complex were grown from a 1:1 methanol-acetonitrile mixture. The crystal structure exhibited a distorted tetrahedral Zn$^{2+}$ center where both the arms of L act as bidentate ligands through their imine nitrogen and phenoxide oxygen to give an N$_2$O$_2$ core where the total complex is neutral. Crystal data for Zn-L is as follows. Empirical formula: C$_{82}$H$_{106}$N$_8$O$_6$Zn; formula. wt.: 1365.16; crystal system: triclinic, P1̄; unit cell dimension (Å): 15.5813(6), 17.3524(5), 18.4381(6), 79.959(3), 65.028(4), 76.432(3); V=4351.7(1) (Å$^3$); Z=2; D$_c$=1.15 (g ml$^{-1}$); unique reflections: 28611, R_obs: 0.068, wR2_obs: 0.205. In the primary coordination sphere about the zinc ion, bond lengths (Å) and bond angles) (° were Zn—O6=1.903(4), Zn—O5=1.911(3), Zn—N4=1.985(3), Zn—N8=1.996(2); N4-Zn—N8=122.1 (1), N4-Zn—O6=118.4(1), N8-Zn—O6=97.6(1), N4-Zn—O5=96.4(1), O5-Zn—O6=106.7(1), O5-Zn—N8=115.9(1), demonstrating a substantially tetrahedral structure.

Example 3

Figure 3A:
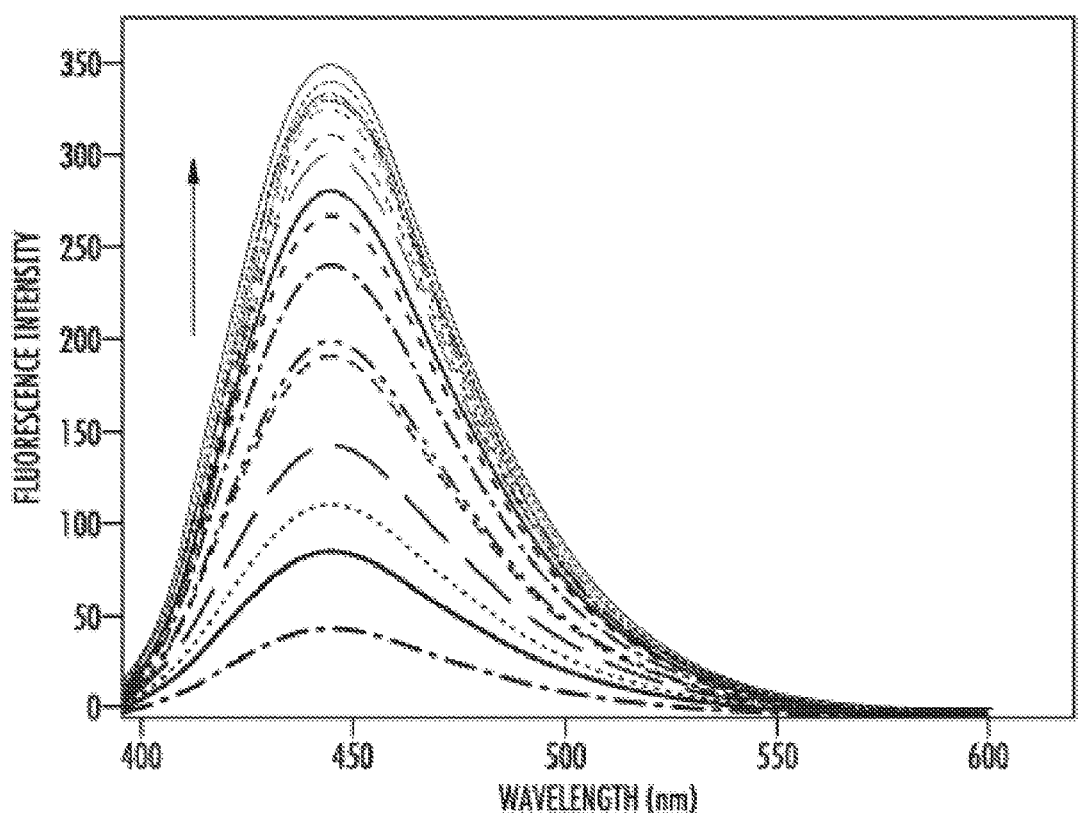
FIG. 3A is the fluorescence spectra of the titration of compound L, with $Zn^{2+}$ in aqueous methanolic (1:4 v/v) HEPES buffer (pH ~7.4), and $\lambda_{ex}$=380 nm.
Figure 3B:
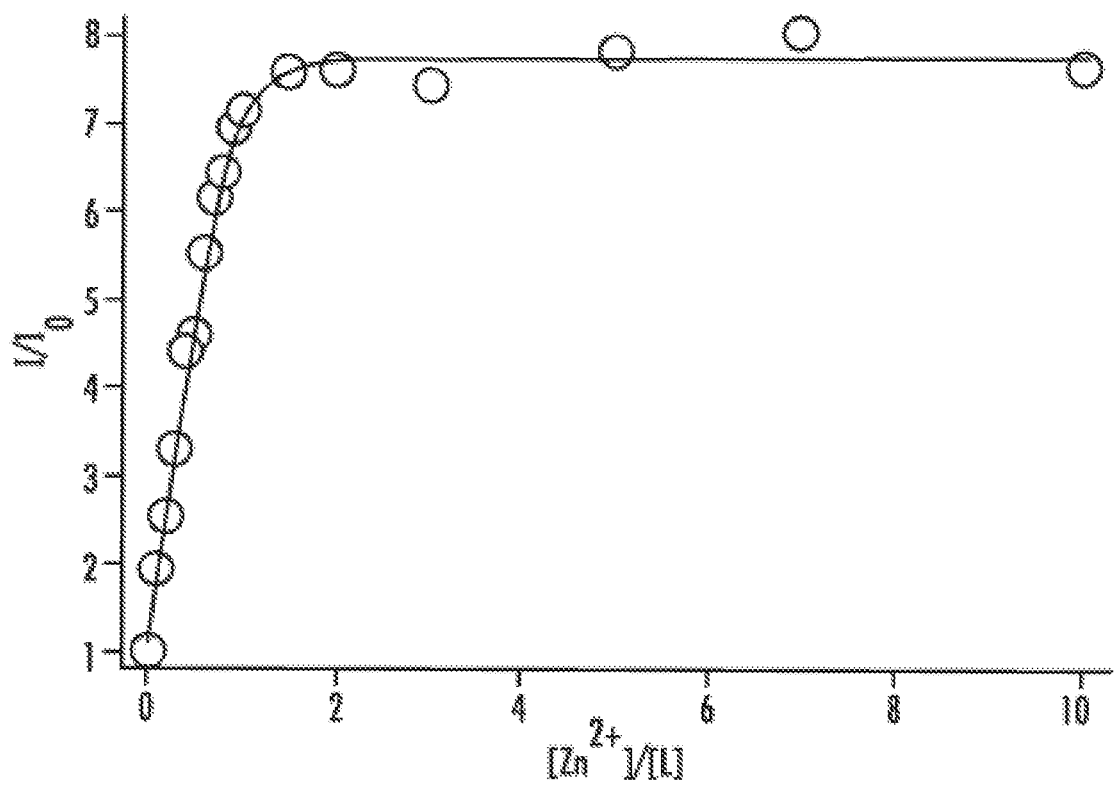
FIG. 3B shows the relative fluorescence intensity ($I/I_0$) as a function of $[Zn^{2+}]/[L]$ and visual color change observed when irradiated at 380 nm, according to Example 1.

Fluorescence titrations. The receptor L exhibits very weak fluorescence emission at about 450 nm when excited at 380 nm in 10 mM methanolic HEPES buffer of pH=7.4 containing 4:1 (v/v) methanol and 50 mM HEPES buffer. Titrating such a solution of L with Zn$^{2+}$, the fluorescence intensity enhances as a function of increasing Zn$^{2+}$ concentration (FIG. 3A). A plot of fluorescence intensity as a function of added [Zn$^{2+}$]/[L] mole ratio (FIG. 3B) shows a stoichiometry of 1:1 between L and Zn$^{2+}$ and exhibits intensity saturation at >1 eq. An association constant of 148537±2930 M$^{-1}$ for the L-Zn complex was derived using Benesi-Hildebrand equation. When excited at 365 nm, the L+Zn$^{2+}$ complex is visibly fluorescent while L is not.

Example 4

Figure 4:
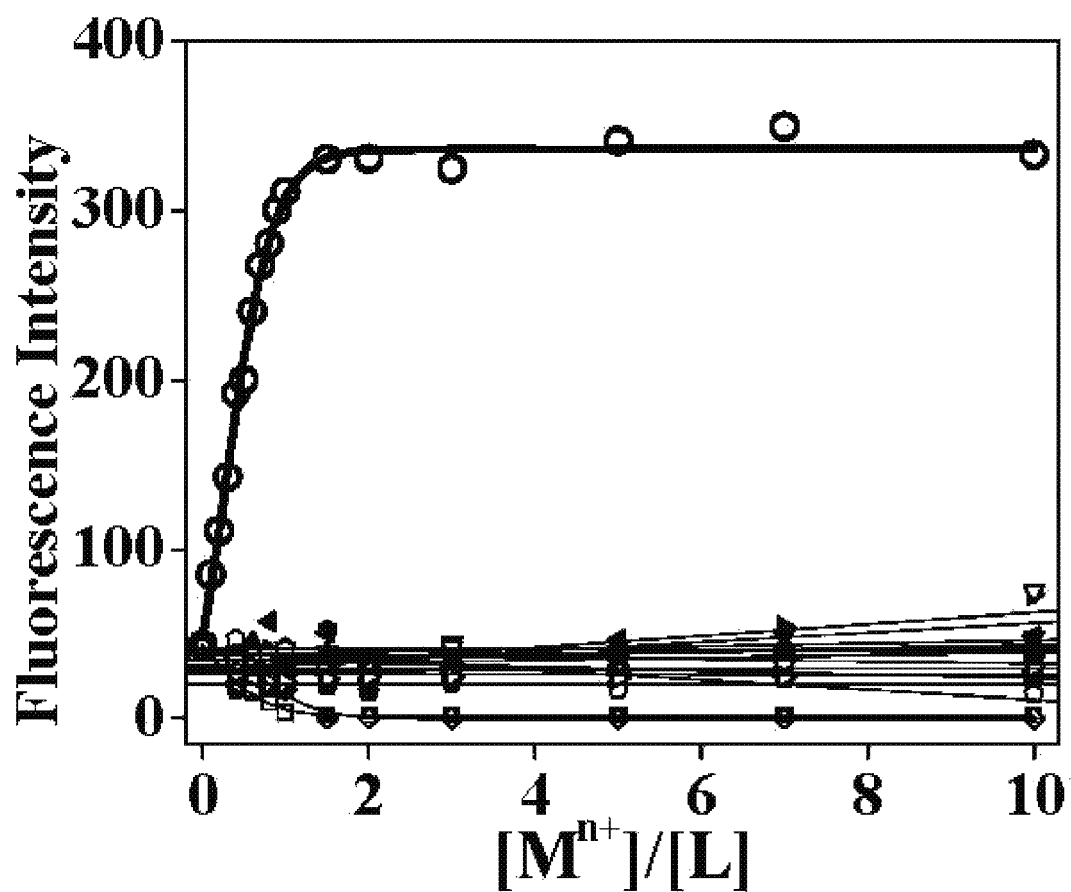
FIG. 4 is a plot of fluorescence intensity as a function of $[M^{n+}]/[L]$ mol ratio for different metal ions, according to the examples.
Figure 5:
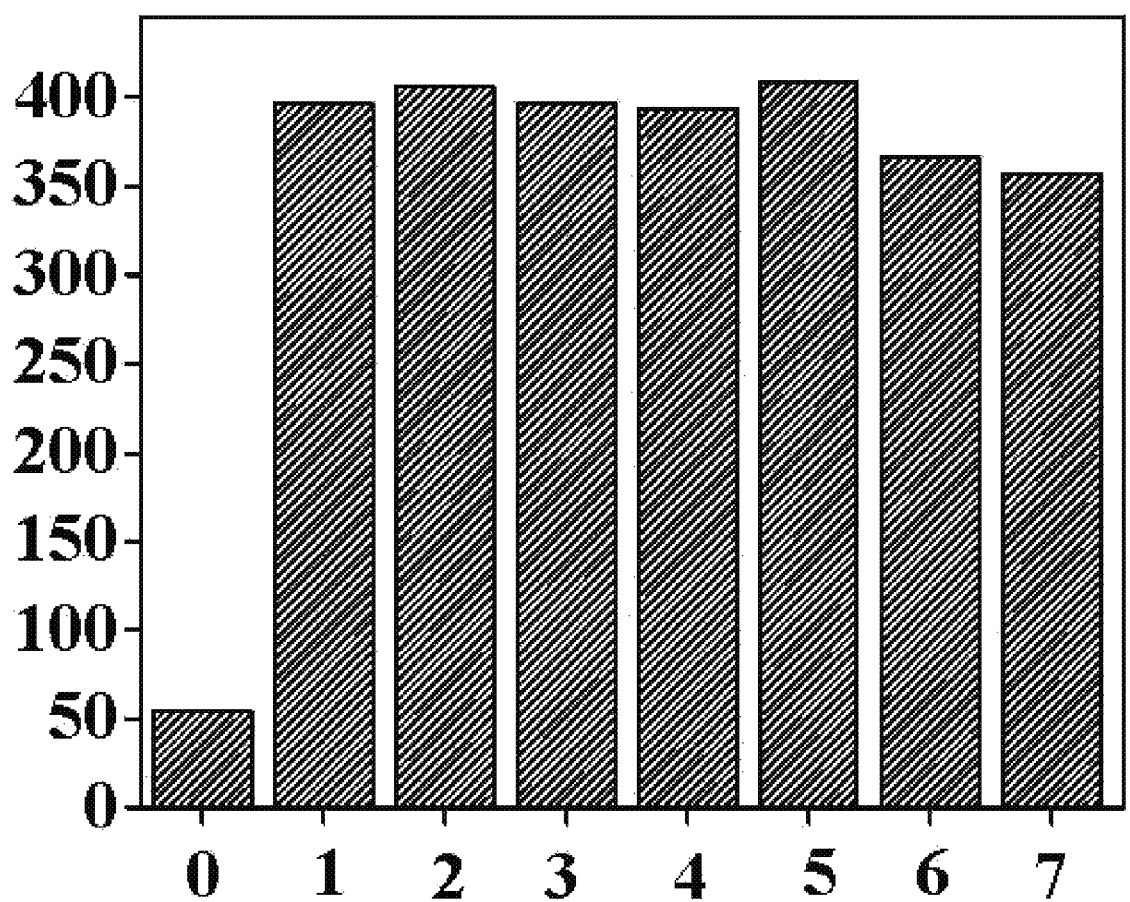
FIG. 5 is a histogram of fluorescence response of various metal ions on the Zn-L complex. (0=L; 1=Zn-L; 2=Zn-L+$Na^+$; 3=Zn-L+$K^+$; 4=Zn-L+$Ca^{2+}$; 5=Zn-L+$Mg^{2+}$; 6=Zn-L+$Cd^{2+}$; 7=Zn-L+$Hg^{2+}$), where 30 equivalents of alkali and alkaline earth metal ions and 10 equivalents of $Cd^{2+}$ and $Hg^{2+}$ were used, according to the examples.

Competitive fluorescence titration in presence of other ions. To test L's ability to selectively detect Zn$^{2+}$, fluorescence titrations were carried out in the same medium with the different metal ions, Li$^+$, Na$^+$, K$^+$, Cs$^+$, Mg$^{2+}$, Ca$^{2+}$, Sr$^{2+}$, Ba$^{2+}$, Nm$^{2+}$, Co$^{2+}$, Ni$^{2+}$, Cd$^{2+}$, Ag$^+$ and Hg$^{2+}$. No significant fluorescence enhancement or quenching in presence of these ions was observed (FIG. 4). Concentration variation titration carried out between L and Zn$^{2+}$, while maintaining their molar ratio at 1:1, resulted in a minimum detection limit of 36 ppb for Zn$^{2+}$ under these conditions. Since biological systems may possess large concentrations of alkali and alkaline earth ions, the selectivity of Zn$^{2+}$ has been studied by carrying out appropriate competitive metal ion titrations. No significant change in the fluorescence enhancement of L with Zn$^{2+}$ was observed. Hence the fluorescence of L with Zn$^{2+}$ does not exhibit changes in presence of other biologically important alkali and alkaline earth metal ions, however, shows strong complexation behavior of towards zinc (FIG. 5). As cadmium and mercury belong to the same period, the selectivity of Zn$^{2+}$ towards L was tested by carrying out the corresponding competitive ion titrations. Again, these ions did not appear to interfere in the detection of Zn$^{2+}$ (FIG. 5). Thus these tests further support L's use for selectively detecting Zn$^{2+}$.

Example 5

Figure 6:
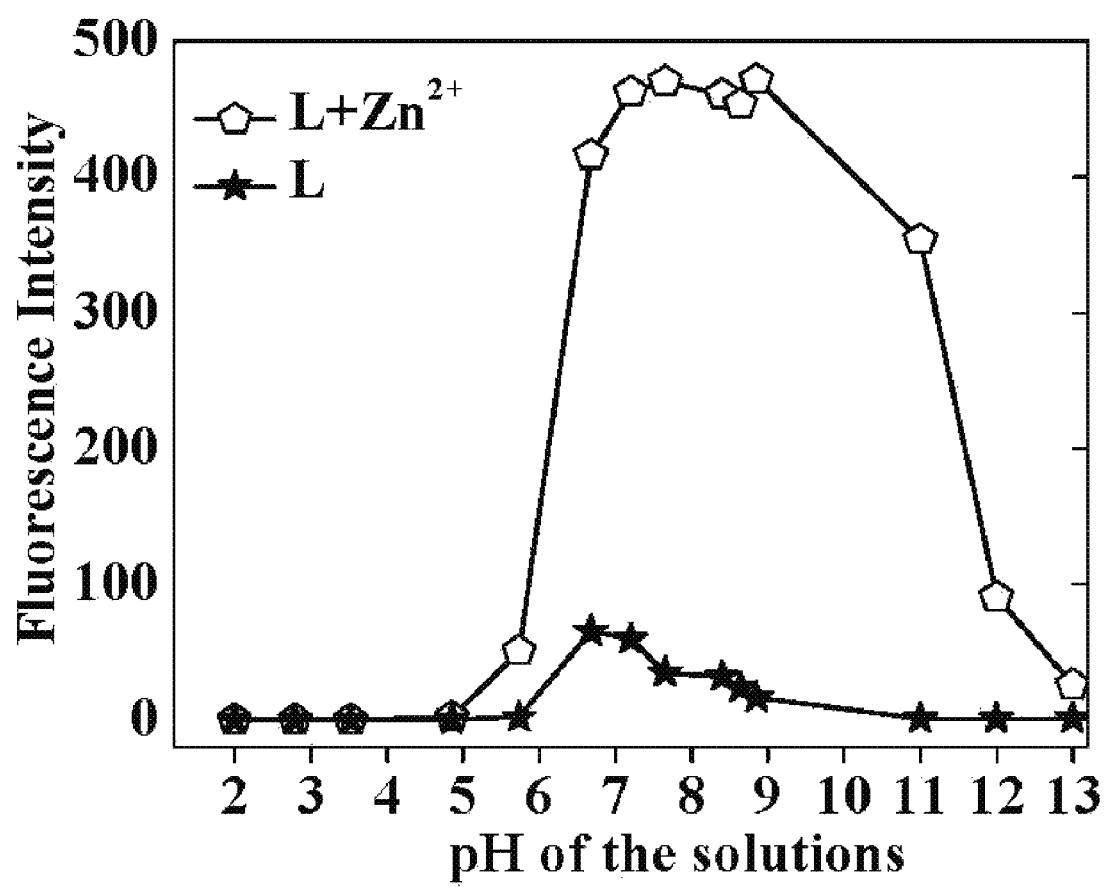
FIG. 6 is a graph of fluorescence intensity for L and L+$Zn^{2+}$ as a function of pH, and according to the examples.

Testing the effect of pH variation on zinc detection. When titrations were carried out between L and Zn$^{2+}$ in the same medium but varying the pH from 6 to 9, no variation in the fluorescence intensity resulted (FIG. 6), suggesting that L can detect Zn$^{2+}$ in this pH range, which mostly covers the physiological systems. While the quantum yield of L is only Φ=0.028, binding of Zn$^{2+}$ to L enhances it to Φ=0.32. The observed ten-fold increase in the quantum yield of L in presence of Zn$^{2+}$, simultaneously in the presence of water and buffer in the medium, and the observed low detection limit demonstrates the usefulness of L for detecting and quantifying Zn$^{2+}$ by switch on fluorescence spectroscopy, even in a biological medium.

Example 6

Biological applicability of Zn$^{2+}$ detection by L. Biological applicability of L to sense Zn$^{2+}$ has been addressed by carrying out fluorescence titrations using blood serum, which includes albumin proteins, and albumins such as human serum albumin (HSA), bovine serum albumin (BSA) and an α-lactalbumin (LA), which are capable of complexing Zn$^{2+}$. Fluorescence experiments were carried out by taking an in situ generated Zn-L complex and titrating this complex with varying concentrations of blood serum or the proteins (HSA, BSA and α-LA). Serum samples were obtained from a healthy volunteer after fasting. The blood sample was allowed to clot and serum was obtained via centrifugation. The serum samples were kept at −20° C. for storage. Serum (100 mL) was dissolved in HEPES buffer (3 mL) and used as stock solution. The bulk solution for proteins had a concentration of 1 mg/mL. Tests in this manner were not carried out beyond this concentration of the serum or the proteins due to precipitation.

Figure 7:
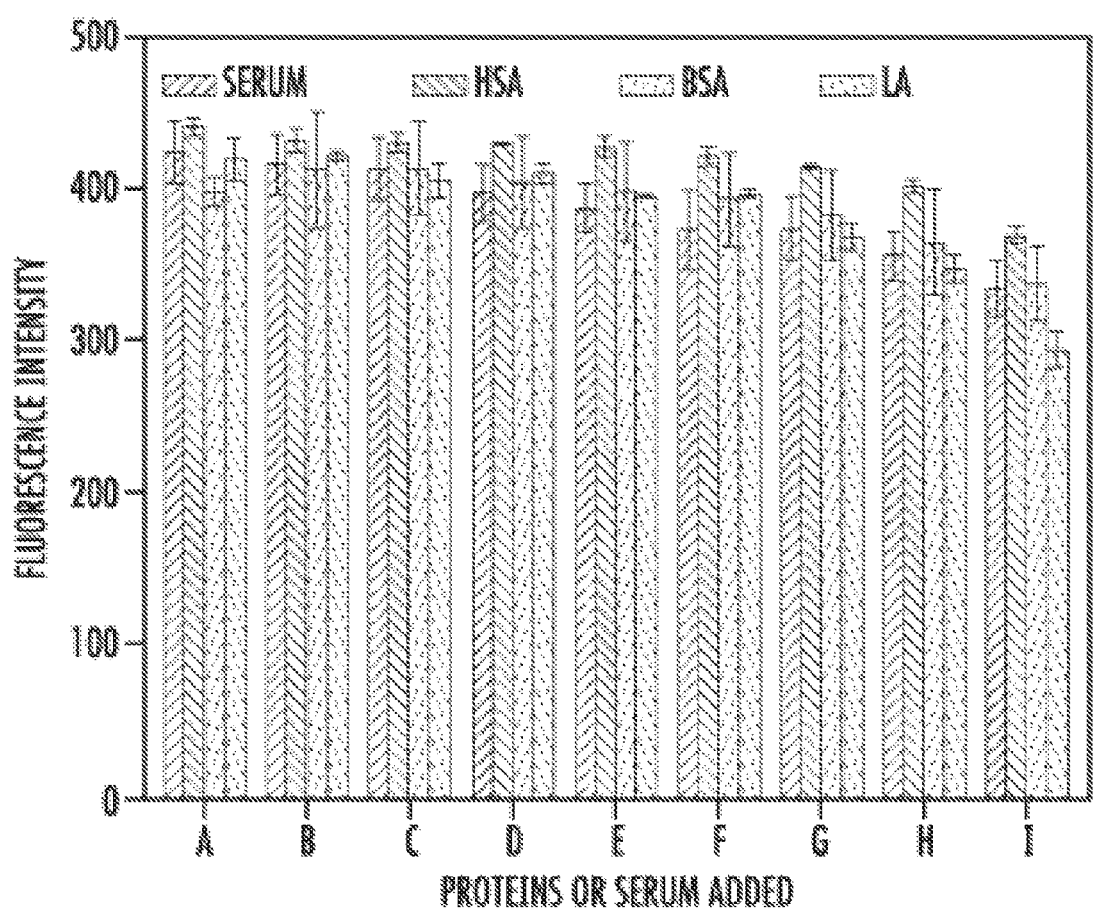
FIG. 7 includes histograms showing the fluorescence response of L (10 mM) with $Zn^{2+}$ (30 mM) in the presence of proteins or serum in aqueous-methanolic HEPES buffer at pH=7.4, where the mixture of L and $Zn^{2+}$ was titrated with varying amounts of either the protein (human serum albumin HSA, bovine serum albumin BSA, or α-lactalbumin LA) (a=0 mL; b=20 mL; c=40 mL; d=60 mL; e=80 mL; f=100 mL; g=150 mL; h=200 mL and i=300 mL) or serum (a=0 mL; b=10 mL; c=20 mL; d=30 mL; e=40 mL; f=50 mL; g=60 mL; h=80 mL and i=100 mL), according to the examples.

Almost no change was observed in the fluorescence intensity of the about 450 nm band of L either in presence of these proteins individually or as a whole in presence of the serum (FIG. 7). Thus L can selectively detect $Zn^{2+}$ even in the blood serum milieu. The lower limit of $Zn^{2+}$ concentration at which L detected $Zn^{2+}$ was found to be 332 ppb in blood serum.

Example 7

Figure 8:
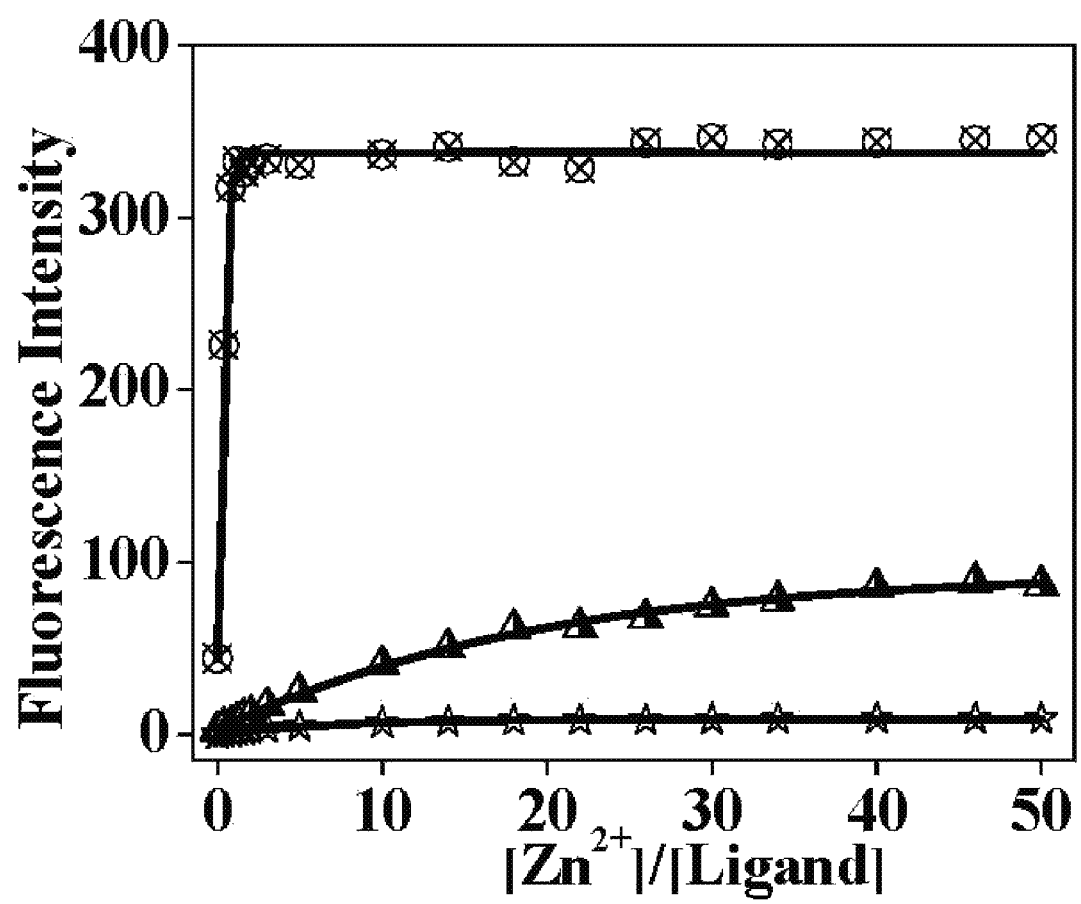
FIG. 8 is a graph of fluorescence intensity as a function of $[Zn^{2+}]/[Ligand]$ mole ratio, where ⊗=L, =$L_3$, and △=$L_a$, according to the examples.

Titrations with the control molecules. The usefulness of the Schiff's base portion as well as the calix[4]arene platform in L for sensing $Zn^{2+}$ was addressed by employing $L_3$ (a precursor that possesses an aldehyde but not an imino group) and $L_4$ (a "single stranded" version of L) as control $Zn^{2+}$ detectors (see Scheme 1). Fluorescence titrations demonstrated that L detected $Zn^{2+}$ selectively, while the control detectors did not (FIG. 8). For $L_3$ and $L_4$, the fluorescence enhancement was found to be very low, and that was only at very high molar equivalents of $Zn^{2+}$, such as, greater than 30 molar equivalents. Thus the receptor molecule, L was much more sensitive toward $Zn^{2+}$ than the control molecules, $L_3$ and $L_4$.

L has been demonstrated to detect $Zn^{2+}$ selectively by switch-on fluorescence. A 1:1 complex between L and Zn has been shown based on fluorescence, absorption, ESI MS and $^1$H NMR. Further, L's selectivity to detect $Zn^{2+}$ has been demonstrated, in aqueous methanolic HEPES buffer, in the pH range of 6-11, in blood serum milieu, in presence, e.g., of albumins, of alkali and alkaline earth ions, and of cadmium and mercury. L has been demonstrated to be selective as compared to its precursor aldehyde derivative, $L_3$, indicating the usefulness of the Schiff's base moiety. L has also been demonstrated to be a more efficient $Zn^{2+}$ detector than $L_4$, a single stranded version of L, indicating the usefulness of the calix[4]arene scaffold for the detection.

EQUIVALENTS

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compounds, compositions, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, or compounds, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Finally, as will be understood by one skilled in the art, a range includes each individual member.

Other embodiments are set forth in the following claims.

What is claimed is:

1. A compound of Formula I:

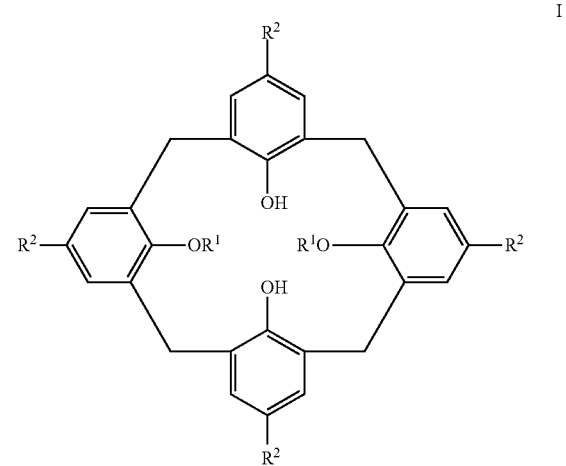

or a salt thereof; wherein: each $R^1$ is a group of Formula:

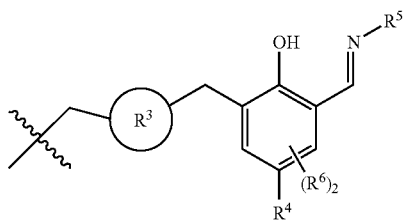

$R^2$ is H, $C_1$-$C_8$ alkyl, or $C_3$-$C_8$ cycloalkyl;
$R^3$ is a 5-membered heteroaryl;
$R^4$ is H or $C_1$-$C_8$ alkyl;
$R^5$ is $C_1$-$C_8$ alkyl or $C_1$-$C_8$ cycloalkyl; and
$R^6$ is H or $C_1$-$C_8$ alkyl.

2. The compound of claim 1, wherein $R^1$ is of Formula:

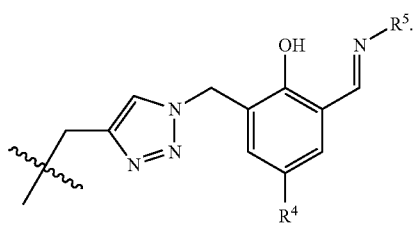

3. The compound of claim 1, wherein $R^2$ is methyl, ethyl, propyl, isopropyl, n-butyl, tert-butyl, amyl, octyl, cyclopropyl, cyclobutyl, cyclopentyl or cyclohexyl.

4. The compound of claim 1, wherein $R^2$ is tert-butyl.

5. The compound of claim 1, wherein $R^4$ is H, methyl, ethyl, propyl, isopropyl, n-butyl, tert-butyl, amyl, octyl, cyclopropyl, cyclobutyl, cyclopentyl or cyclohexyl.

6. The compound of claim 1, wherein $R^4$ is tert-butyl.

7. The compound of claim 1, wherein $R^5$ is methyl, ethyl, propyl, n-butyl, or tert-butyl.

8. The compound of claim 1, wherein $R^5$ is butyl.

9. The compound of claim 1, wherein $R^6$ is H.

10. The compound of claim 1, wherein $R^2$ is tert-butyl and $R^1$ is a group of Formula:

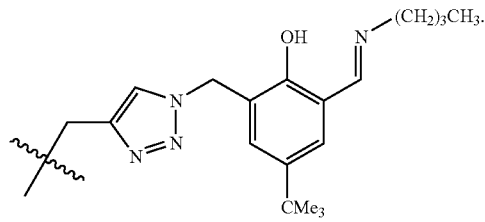

11. A complex comprising the compound of claim 1; and a $Zn^{2+}$ ion.

12. The complex of claim 11, wherein the $Zn^{2+}$ and the compound are present in a 1:1 molar ratio.

13. A method of determining the presence or absence of $Zn^{2+}$ in a solution, the method comprising: contacting the compound of claim 1 with a test sample to form a solution; and recording a fluorescence spectrum of the solution;
wherein:
in the presence of $Zn^{2+}$, the solution exhibits fluorescence intensity at about 450 nm that is greater than a fluorescence intensity of a solution that contains the compound but does not contain $Zn^{2+}$, thereby determining the presence or absence of $Zn^{2+}$ in the solution.

14. The method of claim 13, wherein the test sample comprises serum.

15. The method of claim 13, wherein the test sample comprises aqueous methanolic (4-(2-hydroxyethyl)-1-piperazineethanesulfonic acid (HEPES) buffer.

16. The method of claim 13, wherein a pH of the test sample is from about 6 to about 9.

17. The method of claim 13 that is selective for determining the presence of $Zn^{2+}$ in the presence of other metal ions in the sample.

18. The method of claim 17 that is selective for determining the presence of $Zn^{2+}$ in the presence of $Hg^{2+}$, $Cd^{2+}$, $Li^+$, $Na^+$, $K^+$, $Cs^+$, $Mg^{2+}$, $Ca^{2+}$, $Sr^{2+}$, $Ba^{2+}$, $Mn^{2+}$, $Fe^{2+}$, $Co^{2+}$, $Ni^{2+}$, $Cu^{2+}$, or $Ag^+$.

19. A method of synthesis, comprising contacting a compound of Formula II:

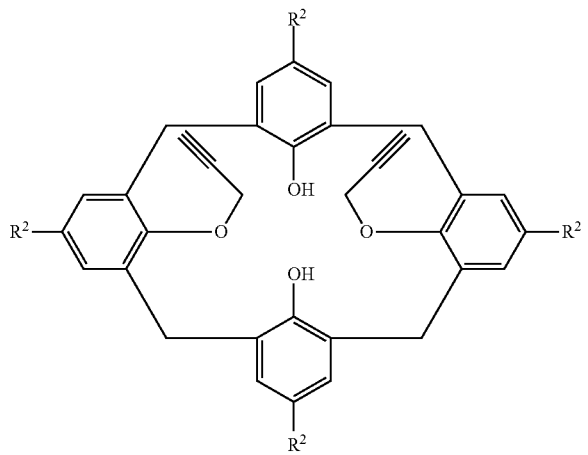

with a compound of Formula III:

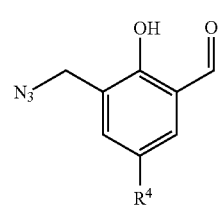

and Cu²⁺ to provide a compound of Formula IV:
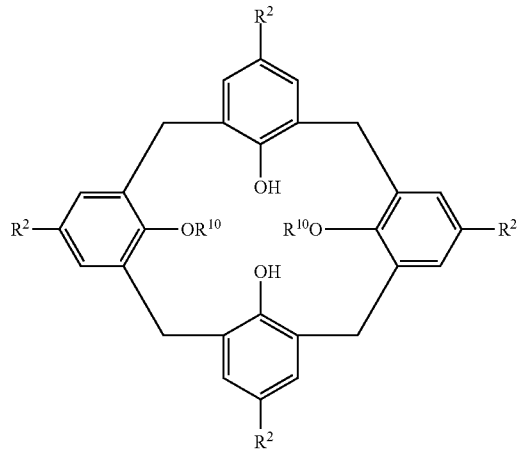
or a salt thereof;
wherein:
R$^{10}$ is
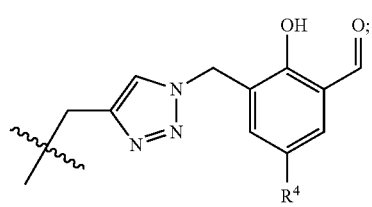
R² is H, C$_1$-C$_8$ alkyl or C$_3$-C$_8$ cycloalkyl; and
R⁴ is H or C$_1$-C$_8$ alkyl.
20. The method of claim 19, further comprising contacting the compound of Formula IV with R⁵NH$_2$, or a salt thereof, to provide a compound of Formula I
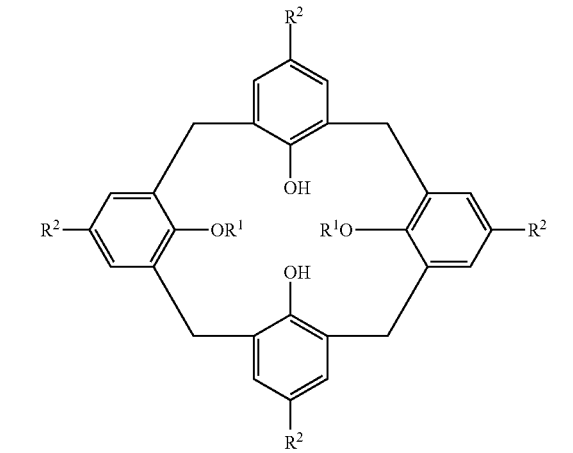
wherein: R¹ is
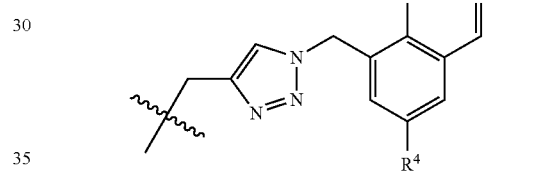
and
R⁵ is C$_1$-C$_8$ alkyl or C$_1$-C$_8$ cycloalkyl.
* * * * *

UNITED STATES PATENT AND TRADEMARK OFFICE
CERTIFICATE OF CORRECTION

PATENT NO. : 8,148,158 B1
APPLICATION NO. : 13/023027
DATED : April 3, 2012
INVENTOR(S) : Rao et al.

Page 1 of 2

It is certified that error appears in the above-identified patent and that said Letters Patent is hereby corrected as shown below:

On Page 2, in Item (56), under "OTHER PUBLICATIONS", in Column 1, Line 43, delete "Flourescent" and insert -- Fluorescent --, therefor.

On Page 2, in Item (56), under "OTHER PUBLICATIONS", in Column 2, Line 19, delete "F" and insert -- $F^0$ --, therefor.

In the Specifications:

In Column 4, Line 4, delete "▲ = $Na^+$," and insert -- ▲ = $Na^+$ , --, therefor.

In Column 4, Line 5, delete "$Mn^{2+}$" and insert -- $Mn^{2+}$, --, therefor.

In Column 8, Line 33, delete "(4-(2-" and insert -- 4-(2- --, therefor.

In Column 9, Line 15, delete "$Ca^{2+}$ $Sr^{2+}$," and insert -- $Ca^{2+}$, $Sr^{2+}$, --, therefor.

In Column 9, Lines 17-27, delete "In another embodiment,................
concentration of $Cd^{2+}$." and insert the same at Line 16, after "or $Cd^{2+}$." as a continuation.

In Column 9, Line 22, delete "$Ca^{2+}$ $Sr^{2+}$," and insert -- $Ca^{2+}$, $Sr^{2+}$, --, therefor.

In Column 9, Line 23, delete "$Co^{2+}$, or" and insert -- $Cu^{2+}$, or --, therefor.

In Column 10, Line 23, delete "—NHRx" and insert -- —$NHR^x$ --, therefor.

In Column 10, Line 24, delete "Rx" and insert -- $R^x$ --, therefor.

In Column 10, Line 25, delete "Rx" and insert -- $R^x$ --, therefor.

Signed and Sealed this
Third Day of July, 2012

David J. Kappos
*Director of the United States Patent and Trademark Office*

In Column 12, below "Chemical Structure L & L₄", delete " 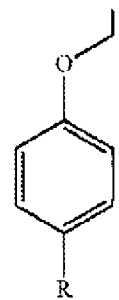 ".

In Column 13, Line 30, delete "CCH)," and insert -- C≡CH), --, therefor.

In Column 15, Lines 35-36, delete "tetracordinated" and insert -- tetracoordinated --, therefor.

In Column 15, Lines 57-58, delete "angles) (°"" and insert -- angles (°) --, therefor.

In Column 16, Line 7, delete "at>1" and insert -- at≥1 --, therefor.

In Column 16, Line 19, delete "$Nm^{2+}$" and insert -- $Mm^{2+}$ --, therefor.

In the Claims:

In Column 20, Line 16, in Claim 15, delete "(4-(2-hydroxyethyl)" and insert -- 4-(2-hydroxyethyl) --, therefor.